(12) United States Patent
Gokaraju et al.

(10) Patent No.: US 8,703,215 B2
(45) Date of Patent: Apr. 22, 2014

(54) **AGENTS FROM *FICUS HISPIDA* FOR THE AMELIORATION OF METABOLIC SYNDROME AND RELATED DISEASES**

(75) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Krishanu Sengupta, Vijayawada (IN); Kiran Bhupathiraju, Vijayawada (IN)

(73) Assignee: Laila Nutraceuticals, Vijayawada, IN (US)

( * ) Notice: Subject to any disclaimer, the term of this patent is extended or adjusted under 35 U.S.C. 154(b) by 0 days.

(21) Appl. No.: 13/364,717

(22) Filed: Feb. 2, 2012

(65) Prior Publication Data

US 2012/0128808 A1     May 24, 2012

Related U.S. Application Data

(63) Continuation of application No. PCT/IN2010/000503, filed on Jul. 30, 2010.

(30) Foreign Application Priority Data

Aug. 4, 2009   (IN) ............................ 1853/CHE/2009

(51) Int. Cl.
*A61K 36/00*     (2006.01)
(52) U.S. Cl.
USPC ......................................................... 424/777
(58) Field of Classification Search
None
See application file for complete search history.

(56) References Cited

U.S. PATENT DOCUMENTS

| 2008/0051341 A1 | 2/2008 | Hermansen et al. |
| 2008/0254157 A1 | 10/2008 | Chauhan et al. |

FOREIGN PATENT DOCUMENTS

| WO | 2008086403 A | 7/2008 |
| WO | 2008093848 A | 8/2008 |

OTHER PUBLICATIONS

Mandal et al. Fitoterapia 73 (2002) 663-667.*
Rasayoga S¢gara—Compiled and Translated by Vaidya Pa´ita Hariprapanna J^H, vol. II : Krishnadas Academy, Varanasi, Edn. Reprint, 1998. [This book contains back references from 1000 B.C. to 20th century]. pp. 305-306 (English translation from TKDL).*
International Search Report issued for PCT/2010/00053 dated Apr. 27, 2011.
Ghosh et al., Hypoglycemic Activity of *Ficus hispida* (Bark) in Normal and Diebetic Albino Rats, Indian J. Pharmacol. Aug. 2004, vol. 36(4), pp. 222-225.
Reaven, Banting lecture 1988. Role of insulin resistance in human disease. Diabetes 1988;37:1595-607.
Expert Panel on Detection, Evaluation, and Treatment of High Blood Cholesterol in Adults. Executive Summary of the Third Report of the National Cholesterol Education Program (NCEP) Expert Panel on Detection, Evaluation, and Treatment of High Blood Cholesterol in Adults (Adult Treatment Panel III). JAMA. 2001;285(19):2486-2497.
Wilson et al., Prediction of Coronary Heart Disease Using Risk Factor Categories. Circulation. 1998; 97: 1837-1847.
Berliner et al., Atherosclerosis: Basic Mechanisms. Circulation. 1995; 91: 2488-2496.
Boring et al., Decreased lesion formation in CCR2-/-mice reveals a role for chemokines in the initiation of atherosclerosis. Nature 394, 894-897 (Aug. 27, 1998).
Chavey et al., Matrix Metalloproteinases Are Differentially Expressed in Adipose Tissue during Obesity and Modulate Adipocyte Differentiation. J. Biol Chem. vol. 278, No. 14:11888-96.
Maquoi et al., Modulation of adipose tissue expression of murine matrix metalloproteinases and their tissue inhibitors with obesity, diabetes. Apr. 2002: 51(4): 1093-101.
Nozaki et al., Reduce Uptake of Oxidized Low Density Lipoproteins in Monocyte-derived Macrophages from C36-deficient Subjects. J/ Clin. Invest. vol. 96, Oct. 1995, 1859-1865.
Michael Greenberg et al., Oxidized phosphatidylserine-CD36 interactions play an essential role in macrophage-dependent phagocytosis of apoptotic cells. J. Exp. Med., vol. 203, No. 12, Nov. 27, 2006, 2613-25.
Susztak et al., Multiple Metabolic Hits Converge on CD36 as Novel Mediator of Tubular Epithelial Apoptosis in Diabetic Nephropathy. PLoS Medicine, Feb. 2005, vol. 2: 152-161.
Holvoet et al., Association Between Circulating Oxidized Low-Density Lipoprotein and Incidence of the Metabolic Syndrome. JAMA. 2008;299(19):2287-93.
Masato Furuhashi et al., Fatty acid-binding proteins: role in metabolic diseases and potential as drug targets. Nature Reviews/Drug Discovery, vol. 7: 489-503, 2008.
Thomas et al., The Trp64Arg polymorphism of the b3-adrenergic receptor gene and obesity in Chinese subjects with components of the metabolic syndrome. International Journal of Obesity, 545-551, 24, 2000.
Pischon et al. Plasma adiponectin levels and risk of myocardial infarction in men, JAMA. 2004; 291(14):1730-7.
Theodore O. Johnson et al., Protein tyrosine phosphatase 1B inhibitors for diabetes. Nature Reviews Drug Discovery, 1; 696-709, 2002.

(Continued)

*Primary Examiner* — Amy L Clark
(74) *Attorney, Agent, or Firm* — Kramer Amado, P.C.

(57) ABSTRACT

The invention discloses herbal ingredient(s) derived from *Ficus hispida* comprising herb powder(s), extract(s), fraction(s), pure compound(s) or mixtures thereof and their compositions for alleviating metabolic disorders selected from metabolic syndrome, obesity, diabetes, atherosclerosis, endothelial dysfunction and other metabolic disorders or conditions; the for amelioration of different biological marker proteins and metabolic processes associated metabolic disorders.

16 Claims, 6 Drawing Sheets

(56) References Cited

OTHER PUBLICATIONS

Venable et al., Overexpression of Protein-tyrosine Phosphatase-1B in Adipocytes Inhibits Insulin-stimulated Phosphoinositide 3-Kinase Activity without Altering Glucose Transport or Akt/Protein Kinase B Activation. J. Biol. Chem. 275: 18318-18326, 2000.

Stienstra et al., PPARs, Obesity, and Inflammation. PPAR Res. 2007; 2007: 95974.

Science News, Science Daily, U.S., Nov. 7, 2007 (http://www.sciencedaily.com/releases/2007/11/071106133106.htm) viewed Jan. 31, 2012.

\* cited by examiner

A

B

US 8,703,215 B2

AGENTS FROM *FICUS HISPIDA* FOR THE AMELIORATION OF METABOLIC SYNDROME AND RELATED DISEASES

CROSS-REFERENCE TO RELATED APPLICATIONS

This application is a continuation of International Application Number PCT/IN2010/000503, filed on Jul. 30, 2010. The entire disclosure of the prior application is hereby incorporated by reference herein in its entirety.

FIELD OF INVENTION

The present invention discloses herbal ingredients derived from *Ficus hispida* and their compositions for alleviating obesity, overweight, diabetes, atherosclerosis, arteriosclerosis, cardiovascular diseases, endothelial dysfunction, metabolic syndrome and other metabolic disorders or conditions.

The invention further includes the amelioration of biomarker proteins or molecules, whose expression/production is altered during the metabolic disorder and conditions by the herbal ingredients derived from *Ficus hispida* and their compositions.

The present invention further includes amelioration of metabolic processes such as inhibition of adipogenesis and/or promotion of adipolysis (lipolysis) by the herbal ingredients derived from *Ficus hispida* and their compositions.

The invention also describes the herbal ingredients derived from *Ficus hispida* and their compositions for the prevention, control and treatment of inflammatory diseases.

BACKGROUND OF THE INVENTION

*Ficus hispida* belongs to the family Moraceae. Its habitat is outer Himalaya from Chenab eastwards to West Bengal Assam. Central and South India and the Andaman Islands. The Ayurvedic Pharmacopoeia of India recommends the fruit in jaundice, oedema and anaemia; fruit and root in leucoderma, vitiligo. In Ayurvedic it is known as Kaakodumbara, Kaashtodumbara, Phalgu, Malayu, Malapu and in Unani as Anjir Dashti. The phytochemistry of fruits, seeds and bark of *Ficus hispida* involve phytochemicals like beta-sitosterol, beta-amyrin, n-triacontanyl acetate, gluacol acetate, hispidin, phenanthraindolizidine alkaloid, bergapten and psoralen. A leucocyanin has been isolated from the root; oleanolic acid from the leaves. A norisoprenoid, ficustriol, and the known phenanthroindolizidine alkaloid O-methyltylophorinidine, were isolated from a $CHCl_3$ extract of the leaves and twigs of *Ficus hispida*. O-Methyltylophorinidine showed potent cytotoxic activity when tested against a small panel of human cancer cells, while ficustriol was inactive. The light petroleum extract of *Ficus hispida* yielded 10-ketotetracosyl arachidate which has shown anti-cancer properties.

The leaf extract of *Ficus hispida* is known to be an effective anti-oxidant. The methanolic extract of the leaf was shown to be hepatoprotective, and to be effective as an anti-diarrhoeal. A Chinese medicine is useful for curing piles and constipation, and is made by using root of *Ficus hispida* L. rhubarb, sanguisorba root, sophora fruit, perilla fruit and talcum. The Chinese medicine for curing piles and constipation showed high cure rate, has no toxic side effect and its total effective rate is 100%.

There is however no prior art, to the best of inventors knowledge, relating to the usage of *Ficus hispida* leaf extract or its compositions for alleviating Metabolic Syndrome, obesity, atherosclerosis, diabetes and several other associated diseases or for ameliorating metabolic marker proteins related to metabolic syndrome.

Metabolic Syndrome also known as Syndrome X, insulin resistance syndrome and Dysmetabolic Syndrome is a condition where in a group of diseased states which increase Atherosclerosis, Stroke and Diabetes. Metabolic Syndrome was first described as a cluster of interrelated common clinical disorders, including obesity, insulin resistance, glucose intolerance, hypertension and dyslipidemia [Reaven, (1988) *Diabetes* 37; 1595-1607].

A criteria for diagnosing Metabolic Syndrome was established by "The Adult Treatment Panel-III" (ATP-III) of the National Cholesterol Education Program in 2001 (JAMA (2001), 285; 2486-2497). Five Criteria were selected by this Panel to identify individuals with Metabolic Syndrome including abdominal obesity, impaired fasting glucose, high triglyceride (TG), low HDL cholesterol (HDL-C) concentrations and increased blood pressure. Metabolic Syndrome is diagnosed, if any three of the components are present in an individual.

Obesity has become a global problem and contributes to hypertension, high serum cholesterol, low HDL cholesterol, and hyperglycemia, and it otherwise associates with higher CVD risk. Abdominal obesity especially correlates with metabolic risk factors. Excess adipose tissue releases several metabolites that apparently exacerbate above risk factors.

Hyper triglyceridemia and high density lipoprotein cholesterol (HDL-C), are two closely associated biochemical parameters that are commonly considered as syndrome criteria. Total cholesterol and low-density lipoprotein cholesterol (LDL-C) are considered to be significant risk factors for cardiovascular disease [Wilson P W F, et. al, *Circulation* 1998; 97: 1837-1847].

A lot of research is being carried out over a decade to develop agents to control Metabolic Syndrome. The application of metabolic markers for the control of this syndrome has also been attempted.

PCT Publication W008086403A1 describes the identification and isolation of chromones and novel chromone compositions from plant sources that are effective in enhancing adiponectin production by adipocytes and regulating genes involved in fatty acid biosynthesis. The invention also include methods for the prevention and treatment of a variety of diseases and conditions including, but not limited to insulin resistance, glucose intolerance, hyperglycemia, Metabolic Syndromes, dyslipidemia, and hypertriglyceridemia.

PCT Publication WO08093848A1 discloses a pharmaceutical product containing phosphatidylcholine derived from soybean for oral administration or for oral cavity application, a functional food and an oral composition which can prevent or ameliorate a disorder in the physical function induced by the increase in an inflammation marker, which can reduce the occurrence of Metabolic Syndrome or the risk of a disease and Metabolic Syndrome, and which can maintain or promote the healthy state.

The published US application US20080051341A1 describes a substance having unique chemical structures of bicyclo[3.2.1]octan alone or in a kaurene structure that provides the substances, such as e.g. steviol, isosteviol and stevioside for use both prophylacticly or directly in the treatment of e.g. the Metabolic Syndrome and obesity.

The incidence of metabolic syndrome, obesity, diabetes, atherosclerosis, endothelial dysfunction and other disease conditions associated with metabolic syndrome are on the rise both in the developed countries and in developing countries across the globe. The products mentioned in the above prior art and some other products that are currently being considered address one or two components of metabolic syndrome. None of these products, however, comprehensively address the total array or major array of the disease components associated with the metabolic syndrome. Hence there is great need for new treatments, especially those derived from the natural sources, which can efficiently be used for the prevention, treatment and control of Metabolic Syndrome and several other associated or related diseases.

SUMMARY OF THE INVENTION

The invention discloses herbal ingredients comprising powders, extracts, fractions, enriched fraction or pure compounds derived from *Ficus hispida* or their compositions for the protection and control of metabolic syndrome, obesity, diabetes, atherosclerosis, endothelial dysfunction and other metabolic disorders or conditions; and for amelioration of the production/expression of biological marker proteins associated with obesity, metabolic syndrome and other metabolic disorders which include but not limited to Peroxisome proliferator-activated receptor gamma (PPARγ), Adipose Differentiation Related Protein (ADRP), adipocyte CD36, Macrophage CD36, Monocyte Chemotactic protein (MCP-1), Oxidized LDL (Ox-LDL), adipocyte fatty-acid-binding protein (aP2/FABP4/A-FABP), beta-3 Adrenergic Receptor (β3AR), Perilipin, Adiponectin, Protein tyrosine phosphatase-1B (PTP-1B), Matrix Metalloproteinase-1 (MMP-1), Matrix Metalloproteinase-3 (MMP-3) and Matrix Metalloproteinase-13 (MMP-13); and also for the control of the metabolic processes such as inhibition of adipogenesis and/or acceleration of lipolysis.

In the other primary embodiment the invention provides herbal composition(s) comprising at least one component selected from the extract(s), fraction(s) and compound(s) or mixtures thereof derived from *Ficus hispida* as an active in combination with at least one component selected from biologically active components derived from plants/animals/microorganisms; pharmaceutically or dietetically acceptable active ingredients, vitamins, amino acids, minerals, vehicles, carriers and diluents or mixtures thereof for the prevention, control and/or treatment of at least one metabolic disorder selected from obesity, overweight, diabetes, atherosclerosis, arteriosclerosis, cardiovascular diseases, endothelial dysfunction, metabolic syndrome and other metabolic disorders or conditions; and also for the amelioration/expression of the metabolic marker proteins related to metabolic disorders/conditions.

Various embodiments of the invention relate to a method of treating a patient having at least one symptom associated with Metabolic Syndrome, comprising:
 a) obtaining an extract of *Ficus hispida*; and
 b) administering an effective amount of said extract of *Ficus hispida* to said patient. The at least one symptom associated with Metabolic Syndrome is selected from the group consisting of obesity, low HDL cholesterol, high triglycerides, diabetes, impaired fasting glucose, dyslipidemia, high total cholesterol, atherosclerosis, and hyperglycemia.

In another aspect, the invention describes the agents derived from *Ficus hispida* and their compositions for the prevention, control and treatment of inflammatory diseases.

The present invention also includes the methods for prevention, control and/or treatment of obesity, metabolic syndrome, diabetes, atherosclerosis, endothelial dysfunction and other metabolic disorders or conditions.

DETAILED DESCRIPTION OF THE INVENTION

Figure 1:
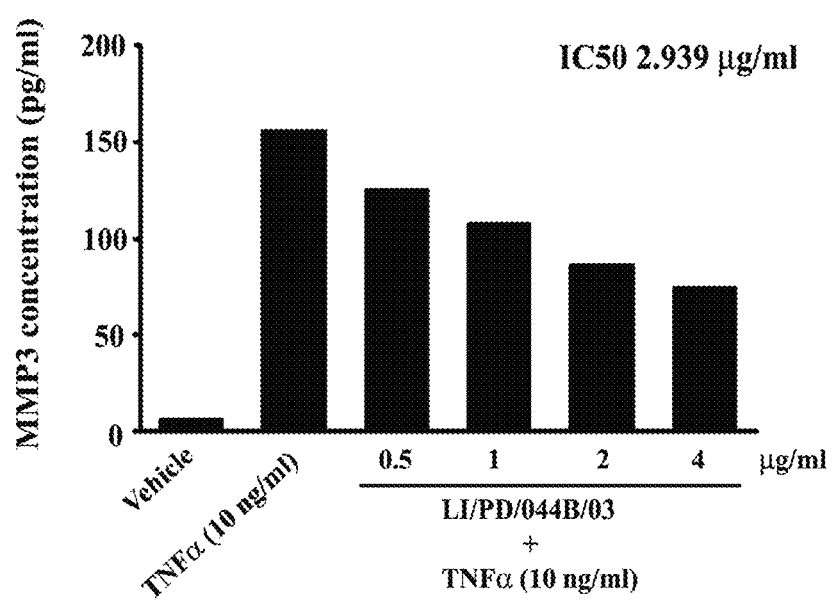
FIG. 1: Illustrates Bar diagrammatic representation of inhibition of MMP3 in SW982 human synovial cells by *Ficus hispida* methanol extract (LI/PD/044B/03). The bars labeled as vehicle, TNFα (10 ng/ml), 0.5, 1, 2 and 4 represent MMP-3 concentrations in SW982 human synovial cell culture supernatants corresponding to cells treated with the vehicle, TNFα (10 ng/ml) for MMP3 induction, *Ficus hispida* methanol extract (LI/PD/044B/03) at 0.5 µg/ml, 1 µg/ml, 2 µg/ml and 4 µg/ml respectively. The IC50 value represents the concentration of *Ficus hispida* methanol extract (LI/PD/044B/03) required to inhibit the MMP3 level by 50%.

As used in this disclosure, a step of obtaining an extract of Ficus hispida encompasses preparation of the extract by extraction with water or an organic solvent from Ficus hispida leaves, Ficus hispida fruit, or other parts of the Ficus hispida plant. A step of obtaining an extract of Ficus hispida further encompasses receiving an extract of Ficus hispida from another party, i.e., purchasing an extract of Ficus hispida from a doctor or pharmacist.

Obesity is excess body weight for a particular age, sex and height as a consequence of imbalance between energy intake and energy expenditure. The primary causes of obesity are either due to overeating, inadequate exercise or eating disorder, some genetic disorders, underlying illness (e.g. hypothyroidism), certain medications or sedentary lifestyle. Obesity increases the risk of many diseases and health conditions such as hypertension, dyslipidemia (for example, high total cholesterol or high levels of triglycerides), type 2 diabetes, coronary heart disease, stroke, gallbladder disease, osteoarthritis, sleep disorders, respiratory problems, tumors (endometrial, breast, and colon), arteriosclerosis and heart failure.

Metabolic syndrome is a condition involving a set of disorders that enhances the risk of heart disease. The major components of metabolic syndrome are excess weight, the cardiovascular parameters (high blood pressure, dyslipidemia, high levels of triglycerides and low levels of HDL in the blood), atherosclerosis, diabetes and insulin resistance. A subject suffering with several of these components, i.e. metabolic syndrome is highly prone to heart disease, though each component is a risk factor.

Adipocytes and macrophages play important role in the pathogenesis of many metabolic syndrome and disease components associated with it. They both share a number of common features, including the ability to phagocytize and kill microorganisms and to secrete cytokines such as tumor necrosis factor (TNF) and interleukin-1 (IL-1). Critical transcription factors in adipocytes involved in regulating the expression of cytokines, inflammatory molecules, and fatty acid transporters are also expressed and have similar biologic roles in macrophages. For example, activation of PPAR, a member of the nuclear-receptor super-family of ligand-activated transcription factors, is associated with differentiation of both types of cells. In adipocytes, PPAR regulates adipocyte development and glucose homeostasis. In macrophages, PPAR regulates expression of inflammatory genes and is involved in the development of atherosclerotic lesions.

The adipocytes, in addition to accumulating fat during the obesity development, produce and circulate several low molecular weight bioactive protein molecules having powerful effects throughout the body. These protein markers are related to different components of metabolic disorders such as obesity and metabolic syndrome. The expression and production of several of these metabolic markers, which include but not limited to PPAR-γ, Adipose Differentiation Related Protein (ADRP), CD36, Adipocyte Fatty-Acid-Binding Protein (aP2/FABP4/A-FABP), Beta-3 adrenergic receptor (β3-AR), adiponectin and Perilipin, become abnormal during obesity and metabolic syndrome and other disease conditions associated with metabolic syndrome.

Atherosclerosis, also known as coronary heart disease (CHD), is one of the major vascular complication and important component of metabolic syndrome. It is a chronic inflammatory reaction to modified lipoproteins, primarily oxidized low density lipoproteins (Ox LDL). Atherosclerosis is thought to develop as a result of lipid uptake by vascular-wall macrophages leading to the development of foam cells and the elaboration of cytokines and chemokines resulting in smooth muscle-cell proliferation (Berliner, J. A., Circulation, 91: 2488-2496, 1995, Boring, L., et. al., Nature, 394: 894-897, 1998). Cluster of Differentiation 36 (CD36) protein has been proven to play a key role in the process of atherosclerosis.

A brief description of some of the metabolic biomarker molecules that are involved in the pathogenesis and control of metabolic syndrome and the disease conditions associated is outlined below:

Adipogenesis:

Adipogenesis is the differentiation and proliferation of pre-adipocytes into major adipocytes or fat cells and it has been one of the most intensely studied models of cellular differentiation. In the adipogenesis process, proliferation of preadipocytes or precursor fat cells is followed by the differentiation of these cells to the mature adipocyte phenotype. The nuclear receptor PPAR γ is expressed predominantly in adipose tissue, where it is known to play a critical role in adipocyte differentiation and fat deposition. Many drugs in the market for the treatment of diabetes type-II, however involve over expression of PPAR γ and promotion of adipogenesis.

Adipocytes secrete proteins exhibiting either beneficial (leptin, adiponectin) or deleterious effects (angiotensinogen). A disturbance in the balance between these various secreted factors, in association with the effect of secretory products from macrophages (cytokines), leads to the development of metabolic syndrome.

Lipolysis:

Lipolysis is the breakdown of stored lipid in adipocytes. β3-Adrenoreceptor agonists can stimulate lipolysis in the white adipose tissue and thermogenesis in the brown adipose tissue. The phytochemical agents having the lipolysis activity could be useful in the treatment of obesity, metabolic syndrome and other metabolic disorders. Adipose tissue lipolysis is the catabolic process leading to the breakdown of triglycerides stored in fat cells and release of fatty acids and glycerol. The proteins involved in the lipolytic process constitute drug targets for the treatment of obesity and the metabolic syndrome.

Matrix Metalloproteinases:

Matrix Metalloproteinases (MMPs) are zinc dependent endopeptidases, that are capable of breaking down all kinds of extra cellular matrix proteins, such as collagen, that are normally found in the spaces between cells in tissues. MMPs are divided primarily into three principal groups, the fibroblast collagenase-1 (MMP-1) formed of the collagenases, the gelatinases comprising gelatinase A (MMP-2) and the gelatinase B (MMP-9), and the stromelysines comprising stromelysine-1 (MMP-3) and matrilysine (MMP-7). An excess of metalloproteinase leads to degradation of biomolecules such as collagen, proteoglycon and gelatin, which can have fatal consequences on epidermis and can also generate diseases of the cartilages, inflammation etc.

MMPs are thought to participate in the pathogenesis of coronary artery disease (CAD), particularly in the occurrence of acute coronary syndrome (ACS). In a study, it was found that MMP and TIMP plasma levels in premature CAD are linked to clinical presentation and markers of inflammation and metabolic disorders rather than to genetic polymorphisms. A systematic review of the literature for clinical studies of several non-traditional biomarkers of atherosclerosis revealed that tissue-remodeling (matrix metalloproteinase-9) and thrombosis (tissue-factor) related biomarkers were consistently elevated in Acute Coronary Syndrome (ACS) compared to stable coronary artery disease (CAD).

The role of MMPs [both positive and negative] in obesity and in the development of adipose tissue has been investigated by several investigators. A few are quoted below: In a study the investigators studied the differential expression of MMPs and TIMPs by Northern blot and real-time PCR in two genetic models of obesity (ob/ob and db/db mice) and in a diet-induced model of obesity (AKR mice). They have concluded that mRNA levels for MMP-2, MMP-3, MMP-12, MMP-14, MMP-19, and TIMP-1 are strongly induced in obese adipose tissues compared with lean tissues [Chavey C et al., *J Biol. Chem.* 2003; 278(14):11888-96]. In a similar study on nutritionally induced obesity mouse, the expression of MMP-3, -11, -12, -13, and -14 and TIMP-1 mRNAs was found to be upregulated when compared to those on the standard diet. It was also observed in an in vitro study that the adipogenesis was reduced in the presence of a synthetic MMP inhibitor [Maquoi E et al., *Diabetes.* 2002; 51(4):1093-101].
Peroxisome Proliferator-Activated Receptor (PPAR)-γ:

Peroxisome proliferator-activated receptor γ (PPAR γ) is a nuclear receptor that plays a pivotal role in obesity and diabetes. An increase in adipose tissue mass can be the result of the production of new fat cells through the process of adipogenesis and the deposition of increased amounts of cytoplasmic triglyceride or lipid droplets per cell. In the adipogenesis process, proliferation of preadipocytes or precursor fat cells is followed by the differentiation of these cells to the mature adipocyte phenotype. PPAR γ is expressed predominantly in adipose tissue, wherein it is known to play a critical role in adipocyte differentiation and fat deposition.
Adipose Differentiation Related Protein (ADRP):

ADRP is a 50 kD protein and it's mRNA (ADRP mRNA), which is 1.7 Kb in size, is expressed at high level in adipose tissue. The expression of ADRP is very low in undifferentiated adipocytes, but ADRP mRNA reaches 50 to 100-fold in few hours after the onset of adipose differentiation process. The above thus indicate the possible role of ADRP in the formation or stabilization of lipid droplets in adipocytes and other cells. ADRP specifically enhances uptake of long chain fatty acids by adipose tissue. Hence ADRP is an important target to identify the compounds that can potentially control obesity and diabetes through regulation of the expression of ADRP.
Adipocyte CD36:

CD36 is a common protein marker expressed by both adipocytes and macrophages. The CD36 expressed in adipocytes is known to function as a fatty acid transporter (FAT). It is a scavenger receptor that binds and internalizes oxidized LDL (Ox LDL) in macrophages. CD36 also functions as a long-chain fatty acid (LCFA) transporter to facilitate the uptake of LCFAs in adipocytes. The CD36 expression is up-regulated by PPAR during the differentiation of both types of cells. It is also shown that the adipocytes can endocytose and lysosomally degrade Ox LDL, a process mainly mediated by CD36. The CD36 null animals thus showed significant decrease in binding and uptake of oxidized low density lipoprotein and showed significant increase in fasting levels of cholesterol, nonesterified free fatty acids, and triacylglycerol.
Macrophage CD36:

CD36 is a prototypic member of the class B scavenger receptor family. It is widely expressed on the surface of monocytes and macrophages, and mediates uptake of oxidized low-density lipoprotein (Ox-LDL) [Nozaki, S., J. Clin. Invest. 96: 1859-1865, 1995] as well as to play a role in diverse cellular processes including foam cell formation, fatty acid transport, engulfment and removal of senescent cells, suppression of angiogenesis, and cell-matrix interactions. The CD36-dependent uptake of Ox-LDL has been shown to be critical to cholesterol accumulation and subsequent foam cell formation; activities that likely contribute to the observed involvement of CD36 in mouse models of atherogenesis [Michael E et al, J. Exp. Med., 203: 2613-25, 2006]. As such it can be an important risk factor of cardiovascular disease and a potential molecular maker of atherosclerosis. Hyperglycemia-induced synthesis of CD36 in macrophages has been associated with increased uptake of Ox-LDL by macrophages and foam cell formation in atherosclerotic lesions in people with diabetes (PLoS Medicine, 2: 152-161, 2005].
Leptin:

Leptin plays an important role in regulating energy expenditure in response to food intake. It is an important adipocytokine of adipose tissues, which further contain low and medium molecular weight proteins like adiponectin, tumor necrosis factor-alpha (TNF-alpha), interleukin-6 (IL-6), resistin, plasminogen-activating inhibitor-I (PAI-1), and angiotensinogen. Together these cytokines play an important role in the adipose tissue physiology and are believed to be a link between obesity, insulin resistance and endothelial dysfunction.
Oxidized LDL:

LDL cholesterol which is known as bad cholesterol becomes more dangerous when it is oxidized. Oxidized LDL can produce inflammation in arteries that supply blood to various organs and tissues. This leads to atherosclerosis and increases the risk of heart attack or stroke. The increased concentration of oxidized LDL was associated with increased incidence of metabolic syndrome overall, as well as its components of abdominal obesity, hyperglycemia, and hypertriglyceridemia. [Holvoet P et al., JAMA. 2008; 299(19):2287-93].
Fatty-Acid-Binding Protein (aP2/FABP4):

FABPs are molecular chaperones linked to metabolic and inflammatory pathways. Different members of the FABP family exhibit unique patterns of tissue expression/distribution and are expressed most abundantly in tissues involved in active lipid metabolism. FABPs play numerous functions. As lipid chaperones, for example, FABPs may actively facilitate the transport of lipids to specific compartments in the cell, such as to the lipid droplet for storage; to the endoplasmic reticulum for signaling, trafficking and membrane synthesis; to the mitochondria or peroxisome for oxidation [Masato, F et al, Nature Reviews/Drug Discovery, Vol. 7: 489-503, 2008]. Adipocytes, however, express significantly higher levels (approximately 10000-fold) of A-FABP than macrophages, upon their differentiation from pre-adipocytes and monocytes respectively. A-FABP is abundantly present in human serum and it may play a central role in the development of major components of the metabolic syndrome such as obesity, type 2 diabetes and cardiovascular diseases, through its distinct actions in adipocytes and macrophages [Masato, F et al, Nature Reviews/Drug Discovery, Vol. 7: 489-503, 2008]. Hence aP2 is an important marker for metabolic disorders β3-Adrenergic Receptor (β3AR):

The body's adrenergic system plays a major part in regulating energy expenditure and lipolysis. The β3AR is the principal receptor mediating catecholamine-stimulated thermogenesis in brown adipose tissue, which in humans is distributed about the great vessels in the thorax and abdomen [Thomas, GN, International Journal of Obesity, 545-551, 24, 2000]. The β3AR is also important in mediating the stimulation of lipolysis by catecholamines in the white fat cells of several species, including humans. Selective agonists of β3ARs are thus potentially useful in treating obesity through enhancing energy expenditure.

Perilipin:

Perilipin is a protein that forms a coating around the lipid droplets in adipocytes. It is a protective coating against body's natural lipases, such as hormone-sensitive lipase, that break triglycerides into glycerol and free fatty acids by a process called lipolysis. Perilipin [PLIN] may play key role in obesity. Following β-adrenergic receptor activation, protein kinase A (PKA) hyperphosphorylates perilipin localized at the surface of the lipid droplet. Phosphorylated perilipin changes conformation and translocate away from the lipid droplet, exposing the stored lipids to hormone-sensitive lipase-mediated hydrolysis of triglycerides (lipolysis) to release nonesterified fatty acids (NEFA). Perilipin is thus an important regulator of lipid storage, lipolysis and energy balance and is an important target for developing anti-obesity drugs.

Adiponectin:

Adiponectin is an important adipokine and it was proved that low levels of adiponectin are associated with disease states such as obesity, diabetes and cardiovascular disease. Administration of adiponectin was proved to be beneficial in animal models of diabetes, obesity and atherosclerosis. High plasma concentrations of adiponectin were also found to associate with lower risk of Myocardial Infarction in men. [Pischon T et al., JAMA. 2004; 291(14):1730-7]. Adiponectin is considered to have antiobese, antidiabetic and anti-atherogenic effect, whereas increased leptin level in blood in obesity is associated with regulation of appetite, energy expenditure, lipids and carbohydrates metabolism, cellular differentiation. The leptin to adiponectin ratio (Lep/AdipoR) in the blood was significantly higher in obese patients in comparison to people with normal BMI and it can be used as additional index in evaluation of obesity complications such as insulin resistance and endothelial dysfunction.

Hence supplements of natural or synthetic origin that enhance the adiponectin levels can have beneficial effects on obesity, diabetes, cardiovascular system and metabolic syndrome and other disease components associated with metabolic syndrome.

Protein Tyrosine Phosphatase 1B (PTP-1B):

Resistance to the hormone insulin is the hallmark of type 2 diabetes and obesity. Protein tyrosine phosphatase 1B (PTP-1B) is regarded as a negative regulator of insulin signal transduction in insulin sensitive cells such as adipocytes, muscle cells and hepatocytes. In insulin resistant diabetes and obesity, the PTB-1B is over expressed and its enzyme activity is increased. Over expression of PTP1B decreases insulin receptor and IRS-1 Phosphorylation and thus produces insulin resistance (Theodore O. J., et al., Nature Reviews Drug Discovery, 1; 696-709, 2002; Carol L. V., et. al., J. Biol. Chem. 275: 18318-18326, 2000). Therefore, agent(s) providing PTP-1B inhibition has become an emerging therapeutic promise to patients, who are at risk to obesity and/or type-2 diabetes.

Metabolic Syndrome is recognized as an important disease that can be single or can be a set of diseased conditions, such as obesity, diabetes and atherosclerosis. If left untreated, it can leads to several complications. Even though several classes of drugs are available in the market for the treatment of different components of Metabolic Syndrome and many of them are associated with a number of side effects, very few medicines are available to treat Metabolic Syndrome and none of them are comprehensive in addressing all the associated diseases. Hence there exists a great medicinal need for developing the protection and treatment against metabolic syndrome, obesity, diabetes and atherosclerosis especially using safe and beneficial natural compounds.

One of the key developments in obesity research in the past decades has been the general recognition that obesity is a chronic low level inflammation. The link between obesity and inflammation has been obvious from the increased plasma levels of several inflammatory markers including cytokines (TNFα, IL-6) and acute phase proteins like C-reactive protein (CRP) in obese individuals (Stienstra R., et. al., 2007, article ID 95974). Thus obesity, diabetes and atherosclerosis as well as other components of the metabolic syndrome have been casually linked to inflammation. It has also been theorized in recent years that chronic, low-grade tissue inflammation related to obesity contributes to insulin resistance, the major cause of Type 2 diabetes (Science News, *Science Daily*, U.S., Nov. 7, 2007).

The research activity in the area of metabolic disorders has been a high priority target for numerous scientists around the world. There is a special interest in finding alternative solutions, especially those based on products of plant origin, as the plant derived products are considered to be natural and safe, in contrast with the commercial drugs of synthetic origin. Keeping this in mind and in conjunction with the urgent need for the prevention, control and treatment of metabolic syndrome, obesity, diabetes, atherosclerosis and endothelial dysfunction and other disease conditions related to metabolic disorders, the inventors have conducted extensive research investigation involving several in vitro and in vivo experiments on several plant extracts, fractions and pure compounds. It was found accidentally that administration of one or more of the components selected from the extracts, fractions, active compounds derived from the herb *Ficus hispida* in a therapeutically effective amount in cell based studies potently ameliorated metabolic processes which include inhibition of adipogenesis and also promotion of adipolysis (lipolysis).

For the purpose of this invention, the phrase/word "herbal ingredient(s)", 'components' and 'agents' widely used in the specification and claims of the present invention refer to at least one selected from the herbal extract(s) fraction(s) and compound(s) or mixtures thereof derived from *Ficus hispida* and the same may be appreciated as such by the person skilled in the art.

From the foregoing, it is evident that the herbal extract(s) fraction(s) and compound(s) or mixtures thereof derived from *Ficus hispida* or their compositions can be used as potential pharmaceutical/dietary supplement/food ingredient for the prevention, control and/or treatment of at least one metabolic disorder selected from obesity, overweight, diabetes, atherosclerosis, arteriosclerosis, cardiovascular diseases, endothelial dysfunction, metabolic syndrome and other metabolic disorders or conditions. The phrase "biologically active components" refers to extract(s) or fraction(s) or compound(s) derived from plants, animals and microorganisms.

The extract(s) or fraction(s) or mixtures thereof as described in the present invention may optionally be in the form of anhydrous or concentrated or reconstituted extract(s) or fraction(s).

The inventors also found unexpectedly that the administration of one or more of the components selected from the extracts, fractions, active compounds derived from the herb *Ficus hispida* in a therapeutically effective amount in cell based studies potently ameliorated the levels of certain biomarker molecules or biological proteins that are altered during metabolic syndrome, obesity, diabetes, atherosclerosis, endothelial dysfunction and other disease conditions associated with metabolic syndrome.

The efficacy of 40% aqueous methanol extract (LI/PD/044B/02), methanol extract (LI/PD/044B/03) and ethyl acetate extract (LI/PD/044B/06) of the leaves of *Ficus hispida* for the inhibition of lipid accumulation in differentiated adipocytes was assessed in 3T3-L1 mouse pre-adipocyte cells. The inhibition of fat accumulation in the treated cells was compared with the mock treated differentiated adipocytes and percentage inhibition was measured. Surprisingly, the methanol extract (LI/PD/044B/03) of the leaves of *Ficus hispida* showed 52.3% inhibition of lipid accumulation at 1 μg/mL concentration. Other extracts of *Ficus hispida* also potently inhibited the adipogenesis as indicated by their percentage inhibitions of lipid accumulation summarized in Table 1.

Similarly, the pro-lipolytic activity of 40% aqueous methanol extract (LI/PD/044B/02), methanolic extract (LI/PD/044B/03) and ethyl acetate extract (LI/PD/044B/06) of the leaves of *Ficus hispida* was assessed in differentiated/mature adipocytes using 3T3-L1 pre-adipocyte cells. The lipolytic activity was assessed in mature adipocytes as per the procedure of Adipolysis Assay Kit provided by Chemicon International, USA by measuring free glycerol secreted into the culture medium. The percentage increase in glycerol concentration in the sample solutions compared to the control containing the known concentrations of glycerol corresponds to the percentage acceleration of lipolysis by different extracts of *Ficus hispida*. Unexpectedly, all the extracts of *Ficus hispida* significantly enhanced the lipolysis/adipolysis process as summarized in Table 2.

It was also found surprisingly that the methanol extract of *Ficus hispida* (LI/PD/044B/03) potently inhibited the MMP3 production in SW982 human synovial cells. The MMP3 production was induced in SW982 human synovial cells using human TNFα in a cell culture experiment. The treatment of the cells with LI/PD/044B/03 reduced the induced levels of MMP3 towards their baseline values (FIG. 1).

The inventors have also found unexpectedly that the alcohol extract of the leaves of *Ficus hispida* effectively ameliorate the expression/production of several metabolic marker proteins related to metabolic processes. The inventors have evaluated the modulation of metabolic biomarkers Peroxisome proliferator-activated receptor gamma (PPARγ), CD36, adipocyte fatty acid binding protein 4 (FABP4 or aP2), Perilipin, and beta-3 Adrenergic Receptor (β3AR) during adipogenesis process in 3T3-L1 adipocytes by methanolic extract of *Ficus hispida* (LI/PD/044B/03) using an immunoblot assay. Briefly, the mouse pre-adipocyte 3T3-L1 cells under maintenance in Dulbecco's Modified Eagle's Medium (DMEM) were pre-treated with different concentrations of LI/PD/044B/03 for 2 h and the control cells were simultaneously subjected to mock treatment. The cells were incubated with differentiation medium for 48 h. It was followed by treatment with post differentiation medium in presence or absence of LI/PD/044B/03 for further 8 days. Finally, the cells were lysed with the lysis buffer and the protein extracts so obtained were evaluated by immunoblot assay. The detailed experimental protocol is given in the experimental section.

It was found surprisingly that the expression of adipocyte differentiation markers such as Peroxisome proliferator-activated receptor gamma (PPARγ), CD36, Fatty Acid Binding Protein 4 (aP2/FABP4) and intracellular lipid droplet surface associated protein (perilipin) was potently inhibited by LI/PD/044B/03 (FIG. 2) in a dose dependent manner. The down regulation of several marker proteins in LI/PD/044B/03 treated adipocytes suggests that the methanolic extract of *Ficus hispida* exerts multiple beneficial roles in controlling the adipogenic differentiation process; by (1) inhibiting cellular differentiation by down regulating PPARγ, which is a nuclear receptor protein that functions as a transcription factor for regulation of cellular differentiation, development and metabolism. (2) restricting cholesterol ester uptake by inhibiting CD36, which is a class B scavenger receptor involved in lipid uptake, (3) decreasing intracellular adiposity and intracellular lipid transport by reducing FABP4/aP2 level, which acts as a transport protein for long chain fatty acids. Moreover, the down regulation of perilipin in LI/PD/044B/03 treated adipocytes strongly indicates the reduced fat store in the cytoplasm. Perilipin is a protein that coats lipid droplets in adipocytes. It offers protection from the action of hormone-sensitive lipase, which breaks triglycerides into glycerol and free fatty acids for use in metabolism or lipolysis. Therefore it is indicative that methanol extract of *Ficus hispida* provides such a state where the stored lipids are more susceptible to enzymatic break down into glycerol and free fatty acids by thinning the perilipin coat around the lipid filled vesicles.

Figure 2:
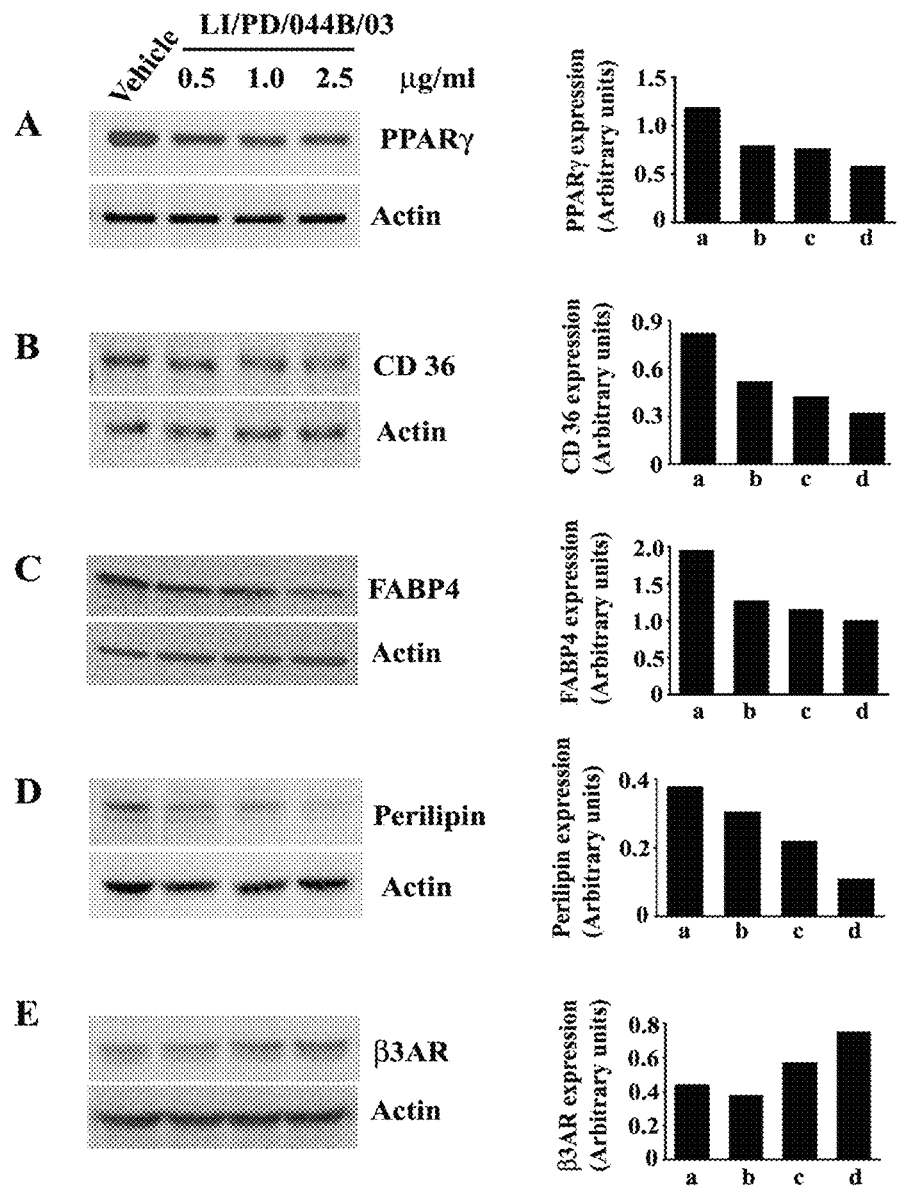
FIG. 2: Illustrates the modulation of marker proteins of adipogenesis and lipolysis processes in 3T3-L1 adipocytes by *Ficus hispida* methanol extract (LI/PD/044B/03). Representative immuno blots indicate down-regulation of various marker proteins such as PPARγ(A), CD36 (B), FABP4 (C), Perilipin (D), and β3AR(E). The 3T3-L1 mouse pre-adipocytes were allowed to differentiate in absence or presence of various concentrations of LI/PD/044B/03 as indicated. Vehicle control cultures received similar concentrations of DMSO only. Expression of actin protein was evaluated in each blot as the internal control. Expression of each protein was measured densitometrically and normalized with actin expression. The comparative levels are represented as bar diagrams (side panels). The bars a, b, c and d represent the levels of marker protein in 3T3-L1 cells treated respectively with vehicle control, 0.5 µg/ml, 1.0 µg/ml and 2.5 µg/ml of LI/PD/044B/03.

In addition, the beta-3 Adrenergic Receptor (β3AR) expression/production in 3T3-L1 adipocytes was significantly enhanced by methanolic extract of *Ficus hispida* (LI/PD/044B/03) in a dose dependent manner as shown in FIG. 2. This is indicative of weight loss through increasing energy expenditure via increasing intracellular cAMP and activation of the mitochondrial uncoupling protein-1 (UCP1) in the adipose tissue. Similarly, the modulation of adiponectin protein by LI/PD/044B/03 in 3T3-L1 adipocytes was evaluated in Western immunoblot assay. The cell culture, treatment protocol and immunoblot assay methodology were as per the standard protocol as briefly described above for the estimation of metabolic markers. The methanol extract LI/PD/044B/03 showed unexpectedly significant upregulation of adiponectin protein expression in 3T3-L1 mature adipocytes in a dose dependent manner as summarized in FIG. 3. Adiponectin is a hormone secreted by adipocytes. It reduces intracellular triglyceride content and up-regulates glucose uptake by potentiating insulin signaling, thus it provides protection from both adipogenicity and from developing insulin resistant diabetes or type 2 diabetes. Therefore, our finding indicates that methanol extract of *Ficus hispida* (LI/PD/044B/03) provide protection against developing obesity, insulin resistant or Type 2 diabetes and also helps in attenuating endothelial dysfunction disorders as well. LI/PD/044B/03 can also be useful in the treatment and control of above metabolic disorders.

Figure 4:
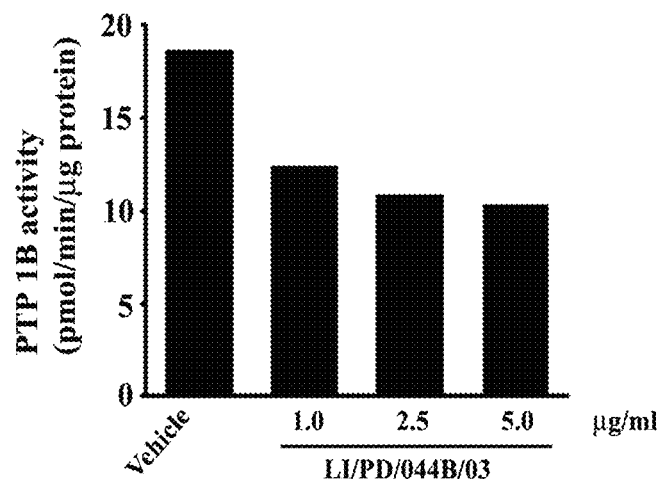
FIG. 4. Illustrates Bar diagrammatic representation of inhibition of PTP1B in 3T3-L1 preadipocytes in a dose dependent manner by *Ficus hispida* methanol extract (LI/PD/044B/03). The enzyme activity (pmol/min/µg protein) was measured calorimetrically by using pNPP substrate in LI/PD/044B/03 treated cells at different concentrations. The bars labeled as vehicle, 1.0, 2.5 and 5.0 represent levels of PTP1B activity in 3T3-L1 preadipocyte cell culture supernatants corresponding to cells treated with the vehicle control (0.1% DMSO), *Ficus hispida* methanol extract (LI/PD/044B/03) at 1.0 µg/ml, 2.5 µg/ml, 5.0 µg/ml respectively.

The effect of LI/PD/044B/03 on insulin sensitivity was further evaluated by studying the modulation of Protein Tyrosine Phosphatase-1B (PTP-1B) activity in 3T3-L1 preadipocytes by methanolic extract of *Ficus hispida* (LI/PD/044B/03). The 3T3-L1 preadipocytes were cultured in Dulbecco's Modified Eagle's Medium (DMEM) as per standard protocol and treated with different concentrations (1.0, 2.5 and 5.0 μg/ml) of LI/PD/044B/03 for 48 h. The cells were lysed with cell lysis buffer and the cell lysates analysed for PTP-1B activity using substrate reagent and the color reaction was read in a microplate ELISA reader (BioRad, USA) as described in the experimental section. The results showed unexpectedly that LI/PD/044B/03 could be a potent inhibitor of PTP-1B activity in 3T3-L1 preadipocytes in a dose dependent manner (FIG. 4).

Protein-tyrosine phosphatase (PTP)-1B acts as a physiological negative regulator of insulin signaling by dephosphorylating the phosphotyrosine residues of the insulin receptor and Insulin receptor-substrate complex 1 (IRS-1). Silencing of PTP-1B gene astonishingly provided resistance from developing type 2 diabetes. Therefore, inhibition of PTP-1B has been recently emerged as a potential target to treat type 2 diabetes. Interestingly, LI/PD/044B/03 exhibited significant inhibition of PTP-1B activity in adipocytes (FIG. 4). This observation further indicates that the methanol extract of *Ficus hispida* can also be used as a potential therapeutic intervention to treat type 2 diabetes.

Figure 5:
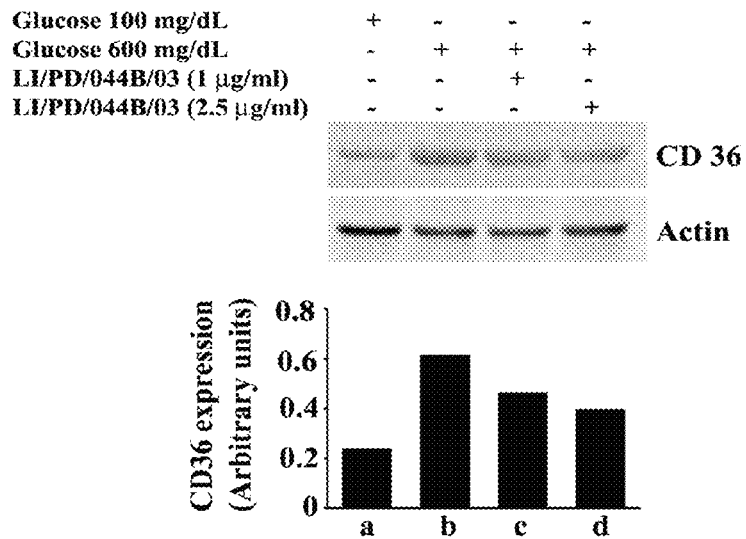
FIG. 5. Illustrates down-regulation of high glucose induced CD36 expression in macrophage cells by *Ficus hispida* methanol extract (LI/PD/044B/03). The J774 mouse macrophage cells were exposed to high glucose (600 mg/dL) for 5 days in presence or absence of LI/PD/044B/03 at various concentrations as indicated. The control cultures received low glucose (100 mg/dL). Representative immuno blot assay demonstrates down regulation of CD36 protein. The expression of actin protein is considered as the internal control. Bar diagram shows the CD36 expression normalized with actin protein (lower panel). Bars a, b, c and d indicate normalized CD36 expression in Low glucose (100 mg/dL) (a); high glucose (600 mg/dL) (b); 1 µg/ml (c), and 2.5 µg/ml (d) of LI/PD/044B/03 treated cultures, respectively.

Atherosclerosis is thought to develop as a result of lipid uptake by vascular-wall macrophages leading to the development of foam cells. In macrophages, CD36 is a scavenger receptor that mediates uptake of oxidized low-density lipoprotein (OxLDL) and subsequent foam-cell development. Therefore, increased level of CD36 in macrophages has been considered as a predictive marker for development of atherosclerosis. In diabetic patients, high rate of atherosclerosis have been associated with increased level of CD36, which provides a strong link between development of atherosclerosis via up regulation of CD36 and hyperglycemia Inhibition of CD36 protein expression in high glucose induced J774 macrophage cells in the presence or absence of LI/PD/044B/03 was evaluated using immunoblot assay. Briefly, equal amount of cell lysates proteins was resolved in 7.5% SDS-PAGE; thereafter, the proteins were transferred to nitrocellulose membrane. After blocking the non-specific sites, the membrane was incubated with CD36 antibody (R&D Systems, Minneapolis, Minn.). Finally, the specific immuno-reactive bands were developed with West-pico chemiluminescent substrate (Pierce Biotechnology, IL, USA), and the immunoblot images were recorded on a Kodak Image Station (Kodak, USA). Band intensities were calculated densitometrically and normalized with expression of actin in respective samples. The results are summarized in FIG. 5. The representative immunoblot image indicated that LI/PD/044B/03 significantly inhibited the CD36 protein expression in high glucose induced J774 macrophage cells. This unexpected observation provides the argument in favor of anti-atherosclerotic properties of methanol extract of the leaves of *Ficus hispida* (LI/PD/044B/03).

Figure 6:
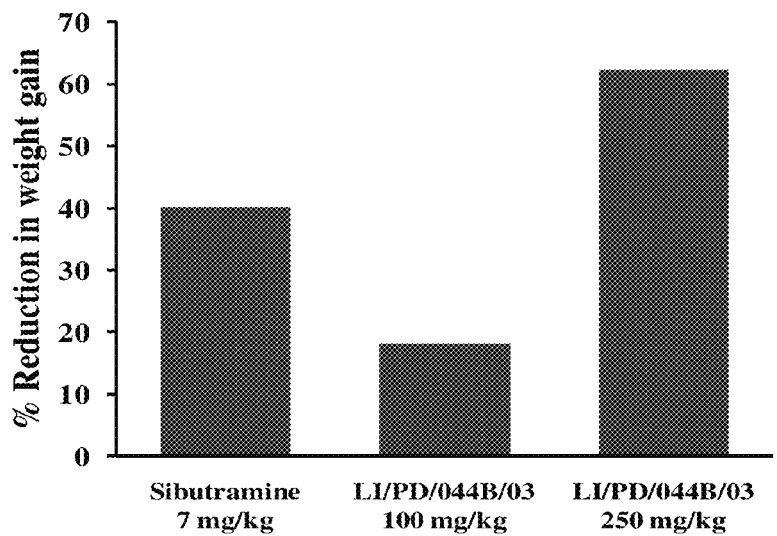
FIG. 6: Bar diagram represents percentage reduction in mean body weight gain in DIO rats compared to control group. The bars represent percentage reduction in mean body weight gain in treatment groups supplemented with sibutramine, LI/PD/044B/03 at 100 mg dose and LI/PD/044B/03 at 250 mg dose.

The potent anti-obesity properties and synergistic effects shown by the extracts of *Ficus hispida* in vitro were put to test in an in vivo model of obesity. Obesity was induced in male Sprague Daley rats by supplementing the rats with High Fat diet for eight weeks. After eight weeks of induction period, the rats were randomly allocated to various groups with seven animals in each group and the animals belonged to the treatment groups were orally supplemented daily either with 100 mg/kg or 250 mg/kg body weight of methanol extract of *Ficus hispda* (LI/PD/044B/03) or 7 mg/kg body weight of sibutramine, each in 10 mL of 0.5% CMC in water for further 8 weeks. The control group of animals received only the vehicle (10 mL of 0.5% CMC in water). Body weight of individual animal was recorded weekly, and mean body weight of the animals in each group was determined. The body weight gain was calculated at the end of 1st week, 4th week and 8th week following initiation of treatment in comparison to their respective initial body weight. LI/PD/044B/03 potently and dose dependently inhibited the body weight gain in treatment group of rats. The rats supplemented with 100 mg and 250 mg/kg body weight of LI/PD/044B/03 exhibited 18.2 and 62.3% reduction in body weight gain respectively in comparison with the control group animals. Similarly, sibutramine at a daily dose of 7 mg/kg exhibited 40% reduction in body weight gain compared to the vehicle treated control group. The results of body weight gain for the treatment groups and control group are summarized in FIG. 6.

Figure 7:
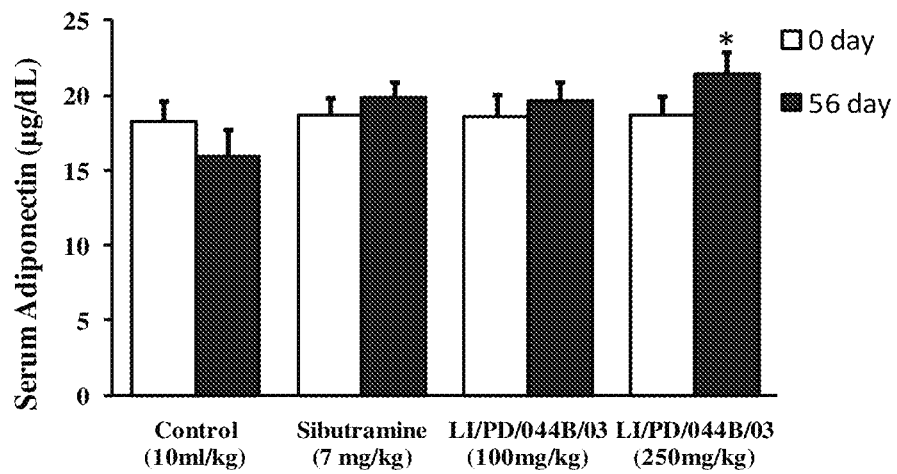
FIG. 7A: Bar diagrammatic representation of increase in serum adiponectin concentration in diet induced metabolic syndrome model of Sprague Dawley rats. Each bar indicates mean±SD of serum adiponectin concentration at 0 day and after 56 days of treatment with either with vehicle (1) or sibutramine or LI/PD/044B/03 (100 mg) or LI/PD/044B/03 (250 mg) as indicated in the diagram. N=6, *indicates statistical significance at p<0.05 (t-test, 8 weeks vs. 0 week).
FIG. 7B: Bar diagram represents serum LDL levels. Each bar represents mean±SD, n=7, *p<0.01 in DIO rats compared to baseline.
Figure 7:
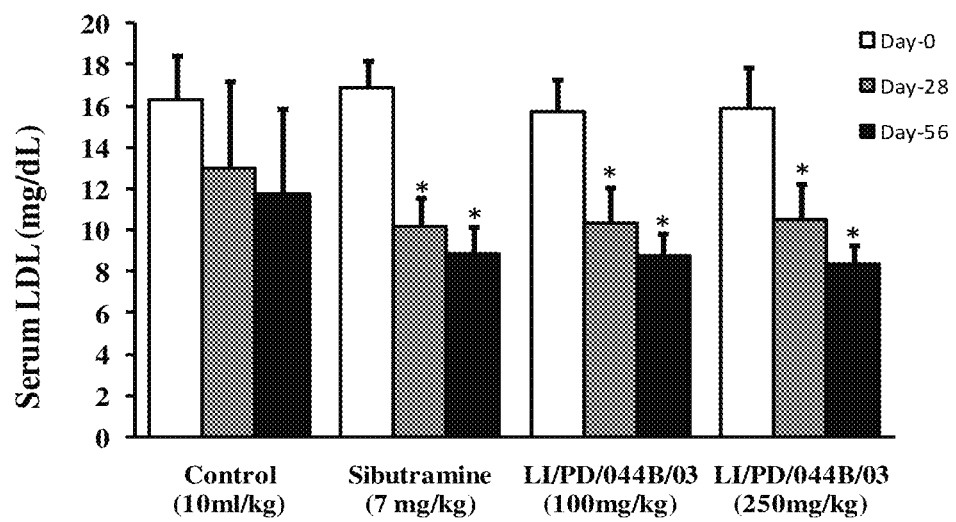

Assessment of serum adiponectin: Adiponectin is a protein hormone exclusively secreted from the adipose tissue, which modulates a number of metabolic processes including glucose homeostasis and lipid metabolism. The circulatory adiponectin concentration is inversely correlated with body fat. Low level of adiponectin is related with obesity, cardiovascular disorder and insulin resistance. Therefore, this protein hormone has been established as a promising marker of metabolic syndrome and disease conditions associated with metabolic syndrome. The serum adiponectin concentration in the treatment and control groups of animals was assessed using double antibody based sandwich rat adiponectin ELISA kit. The data revealed that supplementation of LI/PD/044B/03 at a daily dose of 250 mg/kg body weight for 8 weeks resulted in significant ($p=0.00618$) improvement (14.7%) in serum adiponectin concentration, when compared to the baseline as summarized in FIG. 7A. LI/PD/044B/03 at daily dose of 100 mg/kg body weight also potently improved the serum adiponectin levels (6%). Compared to the control group, the treatment groups supplemented with 100 mg and 250 mg/kg body weight of LI/PD/044B/03 exhibited 23% and 34.5% better improvements respectively, in serum adiponectin concentration. The control group, however, did not show such improvement in serum adiponectin concentration, but it exhibited 12% reduction in serum adiponectin concentration. Hence LI/PD/044B/03 has the potential benefit in alleviating the symptoms such as obesity, cardiovascular disorders, insulin resistant type-II diabetes, metabolic syndrome and other related disorders of metabolic syndrome.

Assessment of serum LDL: Further, the LI/PD/044B/03 treatment also potently reduced the serum LDL levels at both the dose levels as summarized in FIG. 7B.

From the foregoing it is obvious that the invention is unique as the ingredients or the compositions derived from *Ficus hispida* target several metabolic disorders or conditions through modulating multiple mechanisms.

Figure 8:
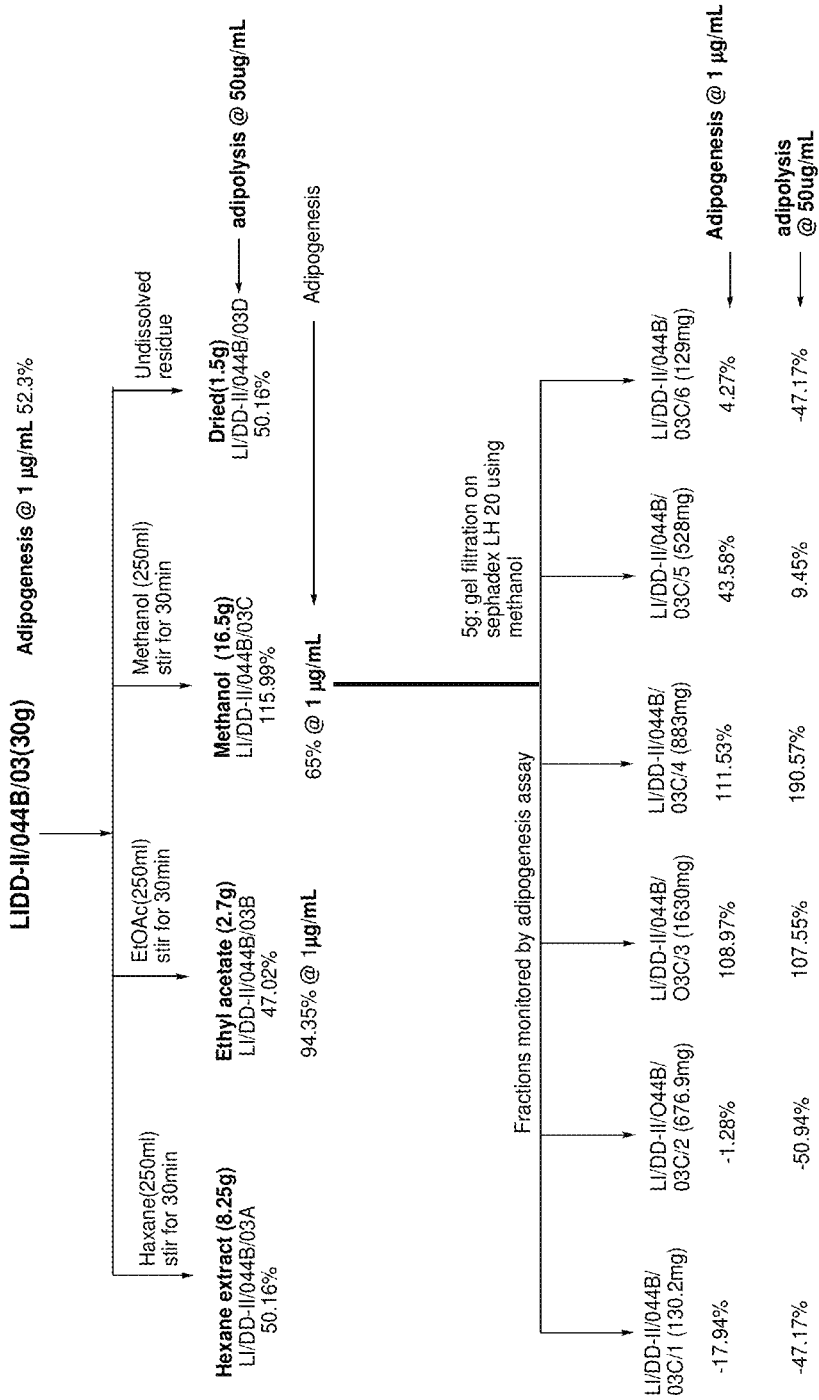
FIG. 8: The flow-diagram for the preparation of active extracts and fractions from Ficus hispida leaf.

As the methanol extract (LI/PD/044B/03) of *Ficus hispida* showed most potent anti-adipogenic activity, LI/PD/044B/03 was fractionated by successively extracting the methanol extract with hexane (250 mL), ethylacetate (250 mL) and methanol (250 mL). The ethylacetate extract (LI/PD/044B/03B) and methanol extract (LI/PD/044B/03C) exhibited potent anti-adipogenesis activity and showed 94.3% and 64.5% inhibition of lipid accumulation respectively in 3T3-L1 mouse adipocyte cells. LI/PD/044B/03B and LI/PD/044B/03C also showed 47% and 116% acceleration of lipolysis respectively in 3T3-L1 mouse adipocytes cells as measured by the percentage increase of glycerol release into the culture medium. The bioactivity guided fractionation of major active extract LI/PD/044B/03C was performed using gel filtration chromatography on LH 20 using methanol as an eluant and the fraction were subjected to biological testing to identify fractions having better anti-adipogenesis and prolipolytic activities. The fractions eluted with methanol were monitored using thin layer chromatography (TLC) and identical fractions were combined to obtain six unique fractions overall that were labeled sequentially as LI/PD/044B/03C/1 to LI/PD/044B/03C/6. Out of these, the fractions LI/PD/044B/03C/3 and LI/PD/044B/03C/4 showed potent anti-adipogenesis activity and prolipolysis activities m 3T3-L1 mouse adipocyte cells. LI/PD/044B/03C/3 and LI/PD/044B/03C/4 showed 109% and 111.5% inhibition of lipid accumulation respectively in differentiated adipocytes at 1 μg/mL concentration. Similarly, fractions LI/PD/044B/03C/3 and LI/PD/044B/03C/4 also showed acceleration of lipolysis by 107.6% and 190.6% respectively in mature adipocytes. These results indicate that the extracts can be fractionated to obtain fractions having better efficacy. The results of the fractionation are summarized in FIG. 8.

It was quite unexpected and surprising to see that a single ingredient derived from *Ficus hispida* could be able to modulate the marker proteins related to many disease conditions associated with metabolic disorders in general and metabolic syndrome in particular. This unexpected result suggests that *Ficus hispida* derived extract(s), fraction(s) and compound(s) can be potential therapeutic agents to prevent, control and/or treat one or more metabolic disorders comprising metabolic syndrome, obesity, diabetes, atherosclerosis, endothelial dysfunction, chronic kidney disease (CKD) and other disease conditions associated with metabolic syndrome in animals and humans.

Further unexpectedly, the methanol extract of the leaves of *Ficus hispida* (LI/PD/044B/03) potently inhibited LPS induced pro-inflammatory cytokine called tumor necrosis factor α (TNFα) in THP-1 human monocytes cells. This important observation in conjunction with potent inhibition of Matrix Metalloproteinase-3 (MMP-3) by LI/PD/044B/03 suggests that the phytochemical component(s) derived from *Ficus hispida* could be useful for the prevention, control and treatment of inflammatory diseases mediated through TNFα and MMP-3.

Even though a few selected extracts have been used in this study, this invention covers herb powder i.e., sterilized dried plant powder, herein after referred as herb powder, all types of extracts, active fractions and active compounds derived from leaves, stems, root, fruits, bark, flowers or mixtures thereof of *Ficus hispida*. Preferably any organic solvent extract or water extract or aqueous organic solvent extract of *Ficus hispida* or a mixture thereof or a fraction or pure compound derived from the extract can be used. The medium for obtaining active extract may be selected from either polar or nonpolar organic solvents or mixtures of organic solvent and water, preferably an organic solvent. The list of organic solvents include but not limited to hexane, dichloromethane, chloroform, ethyl acetate, acetone, methanol, ethanol, n-butanol, iso-propanol, methyl isobutyl ketone etc or the mixtures thereof.

The herb powder or extract(s) or fraction(s) or pure compound(s), herein after referred as herbal ingredient(s) or component(s) derived from *Ficus hispida* may be used as they are for supplementing a human being or an animal in need thereof with an effective dose or they can be optionally combined with a pharmaceutically or dietically acceptable excipients or diluents to obtain their compositions. These compositions may further contain optionally other herbal ingredients selected from anti-obese, anti-diabetic, cardioprotective, anti-atherosclerotic agents or any other ingredient(s) active against other components of metabolic syndrome or other herbal extracts or phytochemicals or mixtures thereof.

The component(s) derived from *Ficus hispida* or their composition(s) are also effective in the amelioration of marker proteins including but not limited to MMP-1, MMP-3, MMP-13, Peroxisome proliferator-activated receptor γ (PPAR-γ), Adipocyte Differentiation Related Protein (ADRP), Adipocyte CD36, Macrophage CD36, Adipocyte fatty acid binding protein (aP2/FABP), beta 3-Adrenergic Receptor (β3AR), Perilipin, Leptin and Adiponectin, which are related to metabolic syndrome and play a role in the prevention of obesity, atherosclerosis and diabetes in mammals or subjects or patients in need thereof. Various exemplary embodiments of the present invention are described below:

In a primary aspect, the invention describes herbal ingredient(s) comprising at least one component selected from the extracts, fractions and compounds or mixtures thereof derived from *Ficus hispida* as an active for the prevention, control and/or treatment of at least one metabolic disorder selected from obesity, overweight, diabetes, atherosclerosis, arteriosclerosis, cardiovascular diseases, endothelial dysfunction, metabolic syndrome and other metabolic disorders or conditions.

In the other primary embodiment the invention provides herbal composition(s) comprising at least one component selected from the extract(s), fraction(s) and compound(s) or mixtures thereof derived from *Ficus hispida* as an active in combination with at least one component selected from biologically active components derived from plants/animals/microorganisms; pharmaceutically or dietetically acceptable active ingredients, vitamins, minerals, vehicles, carriers and diluents or mixtures thereof for the prevention, control and/or treatment of at least one metabolic disorder selected from obesity, overweight, diabetes, atherosclerosis, arteriosclerosis, cardiovascular diseases, endothelial dysfunction, metabolic syndrome and other metabolic disorders or conditions.

In the other important embodiment, the invention provides herbal ingredient(s) comprising at least one component selected from the extracts, fractions and compounds or mixtures thereof and their compositions as described above for the prevention, control and/or treatment of other metabolic disorders or conditions, which include but not limited to hypertension, hypercholesteremia, hyperlipidemia, hypertriglyceridemia, insulin resistance, increased insulin sensitivity, hyperinsulinemia, dyslipidemia, low HDL-cholesterol, lipoprotein aberrations, decreased triglycerides, elevated uric acid levels, fatty liver, non-alcoholic fatty liver disease, polycystic ovarian syndrome, haemochromatosis (iron overload), acanthosis nigricans (dark patches on the skin), impaired glucose tolerance (IGT), impaired fasting glucose (MG) and Type 2 diabetes.

In other embodiment the invention further provides herbal ingredient(s) comprising at least one component selected from the extracts, fractions and compounds or mixtures thereof and their compositions as described above for the amelioration of the expression/production of one or more biological marker proteins related to metabolic disorders or conditions.

In a further embodiment, the invention provides amelioration of the expression/production of one or more biological marker proteins by the herbal ingredient(s) and their compositions as described above, wherein the biological marker proteins comprise Peroxisome proliferator-activated receptor gamma (PPARγ), Adipose Differentiation Related Protein (ADRP), adipocyte CD36, Macrophage CD36, Monocyte Chemotactic protein (MCP-1), Oxidized LDL (Ox-LDL), adipocyte fatty-acid-binding protein (aP2/FABP4/A-FABP), beta-3 Adrenergic Receptor (β3DAR), Perilipin, Adiponectin, Protein tyrosine phosphatase-1B (PTP-1B), Matrix Metalloproteinase-1 (MMP-1), Matrix Metalloproteinase-3 (MMP-3) and Matrix Metalloproteinase-13 (MMP-13).

In other embodiment, the invention also provides herbal ingredient(s) and their compositions as described above for the amelioration of the metabolic processes selected from inhibition of adipogenesis and/or acceleration of lipolysis.

Further embodiment of the invention provides that the percentage of *Ficus hispida* derived component in the composition varies in the range from 0.01% to 99.9%.

Other embodiment of the invention provides that the percentage of *Ficus hispida* derived component in the compositions varies, more preferably in the range of about 0.01 to 90 wt %.

In another embodiment of the invention, the extracts, fractions and compounds derived from the plant parts of *Ficus hispida* are selected from fruits, leaves, flowers, stem, bark, root, hardwood or mixtures thereof.

In other exemplary embodiment, the medium for obtaining active extract may be selected from water, organic solvents or mixtures of organic solvent and water, preferably an organic solvent. The list of organic solvents include but not limited to hexane, petroleum ether, ethylether, dichloromethane, chloroform, ethyl acetate, acetone, acetonitrile, methanol, ethanol, n-butanol, propanol, iso-propanol, methyl isobutyl ketone etc or the mixtures thereof.

In another embodiment of the invention, the fraction(s) and compound(s) derived from *Ficus hispida* is/are obtained using at least one separation technique(s) selected from but not limited to partition(s), precipitation(s), crystallization, normal phase chromatography, reversed phase chromatography, size exclusion chromatography, ion exchange chromatography or combinations thereof.

The other embodiments of the present invention further provide biologically active components for making the herbal composition as described above, wherein the biologically active components are selected from the extracts or fractions or active compounds or phytochemicals or powders derived from plants, animals and microorganisms having any health benefit selected from but not limited to anti-diabetic activity, anti-hyperglycemic activity, hypolipidemic activity, anti-obesity activity, anti-hypertensive activity, anti-platelet aggregation activity, anti-infective activity, anti-atherosclerotic activity and anti-inflammatory activity, anti-oxidant(s) and bio-enhancing activity.

In another embodiment of the invention, the biologically active components as described can be selected further from one or more of extracts/fractions/compounds/derived from *Withania somnifera Salacia reticulata, Terminalia chebula, Zingiber officinale, Azadirachta indica, Tephrosia purpurea, Cinnamon extract, Albizia amara, Amorphophallus campanulatus, Cassia fistula, Cassia tora, Citrullus lanatus, Cyperus rotundus, Gendarussa vulgaris, Holoptelia integrifolia, Piper nigrum, Raphanus sativus* and *Rubia cordifolia*.

In other embodiment, the examples of the biologically acceptable carriers or diluents employed for making the compositions of the present invention comprise surfactants, binders, diluents, disintegrators, lubricants, preservatives, stabilizers, buffers, suspensions and drug delivery systems.

In a further embodiment, the pharmaceutically or dietetically acceptable excipients, carriers and diluents as described above, comprise glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol, propylene glycol and polyethylene glycol, various animal and vegetable oils, white soft paraffin, paraffin and wax.

In a further embodiment, the invention further provides that therapeutically effective amount of the herbal ingredient(s) or the herbal composition(s) as described above can administered be orally, topically, parenterally or by inhalation to a subject or mammal or warm blooded animal in need thereof.

In a further embodiment, the herbal ingredient(s) or herbal composition(s) described above is administered once daily or multiple administrations per day.

Another embodiment of the invention provides the herbal ingredient(s) or herbal composition(s) as described above, wherein said ingredient or composition(s) can be formulated as oral agents such as tablets, soft capsule, hard capsule, soft gel capsules, pills, granules, powders, emulsions, suspensions, syrups, pellets, food, beverages, concentrated shots, drops and the like; and parenteral agents such as injections, intravenous drip and the like; suppositories; and transdermal agents such as patches, topical creams and gel; ophthalmic agents; nasal agents; and food or beverages.

In another embodiment the invention provides that the herbal ingredient(s) or herbal composition(s) as described are delivered in the form of controlled release tablets, using controlled release polymer-based coatings by the techniques including nanotechnology, microencapsulation, colloidal carrier systems and other drug delivery systems.

In a further embodiment, the herbal ingredient(s) or herbal composition(s) as described above can be formulated into or added to existing or new food and beverage form(s) as a healthy food for warm blooded animals.

Various exemplary embodiments of the invention provides a method of preventing, controlling and/or treating one or more metabolic disorders selected from obesity, over weight, diabetes, atherosclerosis, arteriosclerosis, cardiovascular diseases, hypertension, hypercholesterolemia, hyperlipidemia, hypertriglyceridemia, metabolic syndrome, endothelial dysfunction, insulin resistance, increased insulin sensitivity, hyperinsulinemia, dyslipidemia, low HDL-cholesterol, lipoprotein aberrations, decreased triglycerides, elevated uric acid levels, fatty liver, non-alcoholic fatty liver disease, polycystic ovarian syndrome, haemochromatosis (iron overload), acanthosis nigricans (dark patches on the skin), impaired glucose tolerance (IGT), impaired fasting glucose (IFG), hypertension, cardiovascular diseases and other metabolic disorders in a mammal or warm blooded animal in need thereof, wherein the method comprises supplementing the said mammal or warm blooded animal with an effective dose of an herbal ingredient(s) selected from extract(s), fraction(s), active compound(s) or mixtures thereof derived from *Ficus hispida* or their composition as described above.

Various exemplary embodiments of the invention further provides a method of amelioration of the expression or production of at least one biological marker selected from PPAR-γ, C-reactive protein (CRP), Adipose Differentiation Related Protein (ADRP), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin, Protein tyrosine phosphatase 1B (PTP 1B), Matrix Metalloproteinase-1 (MMP-1), Matrix Metalloproteinase-3 (MMP-3) and Matrix Metalloproteinase-13 (MMP-13) in a subject or mammal or warm blooded animal in need thereof, wherein the method comprises supplementing the said subject or warm blooded animals or mammal with an effective dose of a herbal ingredient(s) selected from extract(s), fraction(s), active compound(s) or mixtures thereof derived from *Ficus hispida* or their composition as described above.

Another embodiment of the invention also provides a method of inhibiting adipogenesis and accelerating lipolysis in a mammal, wherein the method comprises supplementing the said mammal with an effective dose of an agent(s) selected from extract(s), fraction(s), pure compound(s) or mixtures thereof derived from *Ficus hispida* or their composition as described above.

In other embodiment, the invention provides a method as described above for alleviating atherosclerosis in a warm-blooded animal.

In other embodiment, the invention provides a method as described above for alleviating metabolic syndrome in a warm-blooded animal.

In other embodiment, the invention provides a method as described above for alleviating diabetes in a warm-blooded animal.

In other embodiment, the invention provides a method as described above for alleviating obesity in a warm-blooded animal.

In a further embodiment, the invention provides herbal ingredients and herbal compositions as described above for use as a pharmaceutical drug/dietary supplement/food ingredient.

Another embodiment of the invention provides the herbal ingredients and herbal compositions as described above, wherein the dosage of said ingredient or compositions ranges from 0.01 to 250 mg/kg body weight/day.

The other embodiment of the invention provides the herbal ingredients and herbal compositions as described above, wherein the dosage of said ingredient or compositions preferably ranges from 0.1 to 50 mg/kg body weight/day.

Various exemplary embodiments of the invention provides the use of herbal ingredient(s) or their composition(s) of present invention as described above for prevention, control and/or treatment of one or more metabolic disorders or conditions including but not limited to obesity, overweight, diabetes, atherosclerosis, arteriosclerosis, cardiovascular diseases, hypertension, hypercholesterolemia, hyperlipidemia, hypertriglyceridemia, metabolic syndrome, endothelial dysfunction, insulin resistance, increased insulin sensitivity, hyperinsulinemia, dyslipidemia, low HDL-cholesterol, lipoprotein aberrations, decreased triglycerides, elevated uric acid levels, fatty liver, non-alcoholic fatty liver disease, polycystic ovarian syndrome, haemochromatosis (iron overload), acanthosis nigricans (dark patches on the skin), impaired glucose tolerance (IGT), impaired fasting glucose (IFG), hypertension, cardiovascular diseases and other metabolic disorders in a mammal or warm blooded animal in need thereof.

Another embodiment of the invention includes herbal ingredients such as the herb powder(s), extract(s) and active fraction(s) and purified compound(s) derived from *Ficus hispida* or their composition(s) for use in therapeutically effective amounts for the alleviation of at least one inflammatory disease condition selected from but not limited to osteoarthritis, rheumatoid arthritis, Alzheimer's disease, asthma, psoriasis, inflammatory bowel syndrome (IBS) and the like.

In another embodiment of the invention, the herb powder(s), extract(s) and active fraction(s) and purified compound(s) of *Ficus hispida* or their composition(s) are useful for the amelioration of at least one inflammatory biomarker protein or molecule including but not limited to TNFα, IL-β, IL-6, MMP-3 and NFκB, whose expression is altered during inflammatory conditions.

The other embodiments of the present invention further provide the usage of the said phytochemical components derived from *Ficus hispida* and its composition(s) as it is or in comminuted form and/or in unmodified form including but not limited to granules and powder The amount of composition that will be effective in the treatment of a particular disorder or condition will depend on the nature of the disorder of the condition, which can be determined by standard clinical techniques. In addition in vitro and in vivo assays may optionally be employed to help identify optimal dosage ranges. The precise dose to be employed in the formulation will depend on the route of administration, and the seriousness or advancement of the diseased condition, and should be decided according to the practitioner and each patient's circumstances. Effective dosages may be extrapolated from dose response curves derived from in vitro or animal model test systems. For example, an effective amount of the composition of the invention is readily determined by administering graded doses of the composition and observing the desired effect.

In another embodiment the invention provides that the product of the present invention is delivered in the form including but not limited to controlled release tablets, using controlled release polymer-based coatings by the techniques including nanotechnology, micro encapsulation, colloidal carrier systems and other drug delivery systems known in the art. The said formulation is designed for once or twice a daily administration.

Another embodiment of the present invention includes, the phytochemical components derived from *Ficus hispida* and its compositions can be formulated into including but not limited to any food and drink form such as solid food like cereals, baby food, chocolate or nutritional bars, semisolid food like cream or jam, or gel. Contemplation was also done to formulate the product of the invention including but not limited to a beverage and the like, such as refreshing beverage, coffee, tea, milk-contained beverage, lactic acid bacteria beverage, drop, candy, chewing gum, chocolate, gummy candy, yoghurt, ice cream, pudding, soft adzuki-bean jelly, jelly, cookie and the like. These various preparations or foods and drinks are useful as a healthy food for the prevention, control and/or treatment of Metabolic Syndrome and related diseases cardiovascular disease, atherosclerosis and diabetes.

In another embodiment of the invention, the percentage of herbal ingredient derived from *Ficus hispida* either individually or in composition varies in the range of 0.01% to 100%. In another embodiment of the invention, the health care food of the present invention comprises the above herbal ingredient derived from *Ficus hispida* or its composition up to 0.01 to 80%, preferably 1 to 50% by weight based on the total weight of the composition. In another embodiment, the invention further comprises, mixing the animal feed with the agents comprising the extract(s) or phytochemical constituents of *Ficus hispida* and its compositions with various components used in the animal feed for the purpose of controlling, preventing and/or treating Metabolic Syndrome associated or related diseases including but not limited to, obesity, diabetes, insulin sensitivity, lipoprotein aberrations, altered triglyceride, impaired glucose tolerance, impaired fasting glucose, insulin resistance, decreased HDL cholesterol, elevated uric acid levels, fatty liver, non-alcoholic fatty liver disease, polycystic ovarian syndrome, haemochromatosis (Iron overload), acanthosis nigricans (dark patches on the skin), endothelial dysfunction, atherosclerosis and cardiovascular diseases.

The following examples, which include preferred embodiments, will serve to illustrate the practice of this invention, it being understood that the particulars shown are by way of example and for purpose of illustrative discussion of preferred embodiments of the invention and they are not to limit the scope of the invention.

EXAMPLES

Example 1

Preparation of Hydroalcohol Extract (LI/PD/044A/02) of Fruits of *Ficus hispida*

Dried fruits of the plant material *Ficus hispida* (1 Kg) was pulverized to coarse powder, extracted with 40% aqueous methanol (6 L) at 80° C. for 1 hr. Extraction process was repeated three times using 40% aqueous methanol (5 L+3 L+3 L). All the hydroalcohol extracts were combined, subjected to fine filtration, and the filtrate was evaporated to dryness on a climbing film evaporator at 50-60° C. under vacuum to obtain the residue (113 g)

Example 2

Preparation of Methanol Extract (LI/PD/044A/03) of Fruits of *Ficus hispida*

Dried fruits of the plant material *Ficus hispida* (1 Kg) was pulverized to coarse powder, extracted with methyl alcohol (5 L) at reflux temperature for 1.5 hr. Extraction process was repeated thrice using methyl alcohol (3 L+3 L+2 L). All the extracts were combined, the combined alcoholic extract was fine filtered, and the clear extract was evaporated to dryness on a rotary evaporator under reduced pressure at 45-50° C. to obtain the residue (97 g).

Example 3

Preparation of Water Extract (LI/PD/044B/01) of Leaves of *Ficus hispida*

Dried leaves of the plant material *Ficus hispida* (1 Kg) was pulverized to coarse powder, extracted with water (6 L) at 80° C. for 1 hr. Extraction process was repeated three times using water (4 L+4 L+2 L). All the extracts were combined, the combined aqueous extract was fine filtered, and the filtrate was evaporated to dryness on a climbing film evaporator at 50-60° C. under vacuum to obtain the residue (110 g).

Example 4

Preparation of Hydroalcohol Extract (LI/PD/044B/02) of Leaves of *Ficus hispida*

Dried leaves of the plant material *Ficus hispida* (1 Kg) was pulverized to coarse powder and extracted with 40% aqueous methanol (6 L) at 80° C. for 1.5 hr. Extraction process was repeated three times using 40% aqueous methanol (5 L+3 L+3 L). All the hydroalcohol extracts were combined, subjected to fine filtration, and the filtrate was evaporated to dryness on a climbing film evaporator at 50-60° C. under vacuum to obtain the residue (143 g).

Example 5

Preparation of Methanol Extract (LI/PD/044B/03) of Leaves of *Ficus hispida*

Dried leaves of the plant material *Ficus hispida* (380 g) was pulverized to coarse powder, extracted with methyl alcohol (3 L) at reflux temperature for 1.5 hr. Extraction process was repeated thrice using methyl alcohol (3×3 L). All the extracts were combined, the combined alcoholic extract was fine filtered, and the clear extract was evaporated to dryness on a rotary evaporator under reduced pressure at 45-50° C. to obtain the residue (34 g).

Example 6

Preparation of Ethyl Acetate Extract (LI/PD/044B/06) of Leaves of *Ficus hispida*

Dried leaves of the plant material *Ficus hispida* (1 Kg) was pulverized to coarse powder charged into a soxhlet extractor and extracted with ethyl acetate (7 L) at reflux temperature for 2 h. The extract was filtered and the spent raw material was re-extracted twice with ethyl acetate (2×5 L) under similar conditions. The combined extract was fine filtered and concentrated under vacuum to obtain a residue (74 g).

Example 7

Inhibition of Matrix Metalloproteinase-3 (MMP-3) Production by Methanolic Extract (LI/PD/044B/03) and 40% Aqueous Methanol Extract (LI/PD/044B/02) of *Ficus hispida* Leaves, and Methanolic Extract (LI/PD/044A/03 and 40% Aqueous Methanol Extract (LI/PD/044A/02) of *Ficus hispida* Fruit Inhibition of MMP-3 production by methanolic extract of *Ficus hispida* was evaluated in TNFα induced SW982 human synovial cells. Briefly, the cells were cultured in DMEM with 2 mM Glutamine, 100 U/mL penicillin, 100 mg/mL streptomycin and 10% fetal bovine serum (Hyclone, Logan, Utah). Five thousand cells per well were seeded into a 96-well cell culture plate (Corning, USA) one day before the experiment. The culture media was replaced with fresh DMEM containing 10% fetal bovine serum. Methanolic extract of *Ficus hispida* (LI/PD/044B/03) was serially diluted in medium, ranging from 0.1 to 10 μg/ml and was pre-incubated with cells for 2 hour in 5% CO2 at 37° C. The MMP3 expression was stimulated in presence or absence of different concentrations of *Ficus hispida* methanol extract (LI/PD/044B/03) with 10 ng/mL human TNFα (R&D System, Minneapolis, Minn.) for 24 hours. The control group was treated with an equal volume of the vehicle only. The supernatant was harvested and the MMP-3 concentration secreted into the cell free culture supernatants was measured using human MMP-3 ELISA Development Kit (R&D System, Minneapolis, Minn., USA). The MMP-3 concentration in culture supernatant was estimated quantitatively by interpolating the optical densities into the standard curve generated from known concentrations of MMP-3. Percentage of MMP-3 inhibition at each concentration of test compound was calculated from the formula: {(Conc. of MMP-3 in IL-1β induced−Conc. of MMP-3 in the test well)×100}÷Conc. of MMP-3 in TNFα induced wells. The data for dose dependent inhibition of LI/PD/044B/03 is depicted in FIG. 1.

The inhibitory concentration for 50% inhibition (IC50) of MMP-3 was calculated from the plot constructed by plotting percentage inhibition against concentration. The methanolic extract (LI/PD/044B/03) of *Ficus hispida* leaf showed an IC50 value of 2.94 μg/mL for MMP-3 production. A similar procedure was repeated with other extracts. *Ficus hispida* leaf extract LI/PD/044B/02, and fruit extracts LI/PD/044A/02 and LI/PD/044A/03 showed 50% inhibitory concentrations (IC50s μg/mL) against Matrix Metalloproteinase-3 (MMP-3) production at 2.45, 2.08 and 2.22 μg/mL respectively.

Example 8

Assessment of Inhibition of Lipid Accumulation in Differentiated Adipocytes by *Ficus hispida* Leaf Ethyl Acetate Extract (LI/PD/044B/06), Methanol Extract (LI/PD/044B/03) and 40% Aqueous Methanol Extract (LI/PD/044B/02), and *Ficus hispida* Fruit Extract (LI/PD/044A/03)

One hundred thousand 3T3-L1 mouse pre-adipocyte cells in Dulbecco's Modified Eagle's Medium (DMEM) containing 10% Fetal Bovine Serum (FBS) were taken into each well of a 24-well plate and incubated for 24 h at 37° C. and 5% $CO_2$. Cells were pre-incubated with different concentrations of LI/PD/044B/03 and then differentiated in a differentiation medium i.e. DMEM containing 500 nM insulin, 1.0 μM dexamethasone, and 0.5 mM isobutylmethylxanthine (IBMX) for 48 h. The cells incubated only with 0.1% DMSO were considered as the vehicle control. Thereafter, the differentiation medium was replaced by DMEM containing 100 nM insulin and cells in presence or absence of different concentrations of LI/PD/044B/03 were incubated further for 8 days. After the treatment period, cells were fixed with 10% buffered formalin for 4 h at room temperature. The fixed cells were stained with Oil Red O solution (0.5 g in 100 ml isopropanol) for 10 min to measure the cellular neutral lipid accumulation. After removing the staining solution, the dye retained in the cells was eluted with isopropanol and OD was measured at 550 nm. The inhibition of fat accumulation in the treated cells was compared with the mock treated differentiated adipocytes. The anti-adipogenic activity of the methanolic extract of *Ficus hispida* (LI/PD/044B/03) is represented by percentage inhibition of lipid accumulation and the data for the inhibition of lipid accumulation at different concentrations of LI/PD/044B/03) is summarized in Table 1.

The percentage inhibition of lipid accumulation caused by ethyl acetate extract (LI/PD/044B/06), 40% aqueous methanol extract (LI/PD/044B/02) and methanol extract of *Ficus hispida* leaf, and *Ficus hispida* fruit extract (LI/PD/044A/03) were also determined using the similar protocol and data is also included in the table.

Example 9

Assessment of Pro-Lipolytic Activity of 40% Aqueous Methanol Extract (LI/PD/044B/02), Methanolic Extract (LI/PD/044B/03) and Ethyl Acetate Extract (LI/PD/044B/06) of *Ficus hispida* Leaf, and *Ficus hispida* Fruit Extract (LI/PD/044A/03) in Differentiated Adipocytes The lipolytic activity was assessed in mature adipocytes as per the procedure of Chemicon International, USA, by measuring free glycerol secreted into the culture medium. One hundred thousand 3T3-L1 Human pre-adipocyte cells in Dulbecco's Modified Eagle's Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium DMEM containing 500 nM insulin, 1.0 μM dexamethasone, and 0.5 mM isobutylmethylxanthine (IBMX) for 48 h. Thereafter, the differentiation medium was replaced by DMEM containing 100 nM insulin and incubated further for 8 days and then the culture medium was removed. The monolayer was washed twice with wash solution (HankOs balanced salt solution), and then 250 μL of incubation solution (Hankés balanced salt solution plus 2% bovine serum albumin) was added to the wells in triplicate in presence or absence of the methanolic extract of *Ficus hispida* (LI/PD/044B/03), and the cells were further incubated for 2 h. To measure lipolysis, 200 μL of free glycerol assay reagent was added to 25 μL of culture supernatants and controls containing glycerol standard. The samples and the controls were incubated for 15 min, and the absorbance was read at 550 nm. A standard curve constructed from the glycerol was used to calculate the concentration of free glycerol in the culture supernatants. The percentage increase in glycerol concentration in the sample solutions compared to the control containing the known concentrations of glycerol corresponds to the percentage acceleration of lipolysis by LI/PD/044B/03. The percentage increase in lipolysis accelerated by LI/PD/044B/03 at different concentration is summarized Table 2.

The percentage increase in lipolysis induced by ethyl acetate extract (LI/PD/044B/06) and 40% aqueous methanol extract (LI/PD/044B/02) of *Ficus hispida* leaf, and *Ficus hispida* fruit extract (LI/PD/044A/03) were measured using the similar protocol and data is also included in Table 2.

TABLE 1

| Name of the test product | Treatment concentration | % inhibition of adipogenesis |
|---|---|---|
| LI/PD/044A/02 | 10 μg/ml | 27.97 |
|  | 25 μg/ml | 120.06 |
| LI/PD/044A/03 | 5 μg/ml | 22.69 |
|  | 10 μg/ml | 80.74 |
|  | 25 μg/ml | 125.71 |
| LI/PD/044B/02 | 0.25 μg/ml | 1.74 |
|  | 0.5 μg/ml | 16.86 |
|  | 1 μg/ml | 40.12 |
|  | 2.5 μg/ml | 99.42 |
| LI/PD/044B/03 | 0.25 μg/ml | 3.49 |
|  | 0.5 μg/ml | 30.23 |
|  | 1 μg/ml | 52.33 |
|  | 2.5 μg/ml | 100.00 |
| LI/PD/044B/06 | 0.5 μg/ml | 21.77 |
|  | 1 μg/ml | 94.35 |

TABLE 2

| Pro-lipolytic activity of *Ficus hispida* | | |
|---|---|---|
| Name of the test product | Treatment concentration | % Acceleration of Lipolysis |
| LI/PD/044A/02 | 50 μg/ml | 37.61 |
| LI/PD/044A/03 | 50 μg/ml | 62.69 |
| LI/PD/044B/03 | 25 μg/ml | 38.35 |
|  | 50 μg/ml | 47.02 |
| LI/PD/044B/02 | 25 μg/ml | 20.64 |
|  | 50 μg/ml | 59.56 |
| LI/PD/044B/06 | 25 μg/ml | 0 |
|  | 50 μg/ml | 47.02 |

Example 10

Inhibition of Peroxisome Proliferator-Activated Receptor Gamma (PPARγ), CD36, Adipocyte Fatty Acid Binding Protein 4 (FABP4 or aP2), Perilipin, and Beta-3 Adrenergic Receptor (β3AR) in 3T3-L1 Adipocytes by Methanolic Extract of Ficus hispida (LI/PD/044B/03)

Experimental protocol: Mouse pre-adipocyte 3T3-L1 cells were maintained in Dulbecco's Modified Eagle's Medium (DMEM) supplemented with 2 mM glutamine, 4.5 g/L glucose and 10% fetal bovine serum. Equal number of cells was plated in each well of 24-well culture plates. Cells were pre-treated with either 0.5 or 1.0 or 2.5 µg/mL of LI/PD/044B/03 for 2 h and followed by addition of differentiation medium containing 500 nM insulin, 1.0 µM dexamethasone, and 0.5 mM isobutylmethylxanthine (IBMX) for 48 h. Thereafter, cells were further incubated with post differentiation medium (DMEM containing 100 nM insulin) in presence or absence of LI/PD/044B/03 for further 3 days. Finally, the cells were harvested, washed with chilled phosphate buffered saline and lysed with the lysis buffer. The protein extracts were clarified at 14,000 g for 20 min. Protein content was measured in Bradford method by using Coomassie blue dye and cell lysates were stored in aliquots at −80° C. until further use. The modulation of adipocyte differentiation markers such as Peroxisome proliferator-activated receptor gamma (PPARγ), CD36, adipocyte fatty acid binding protein (aP2); and intracellular lipid droplet surface associated protein, perilipin expression were evaluated by immunoblot assay. Inhibition of protein expression of biomarker molecules in cell lysates was evaluated using immunoblot assay. Briefly, equal amount of cell lysates proteins were resolved in either 7.5% or 12.5% SDS-PAGE; thereafter, the proteins were transferred to nitrocellulose membrane. After blocking the non-specific sites, the membranes were incubated with either anti-PPARγ, or anti-CD36, or anti-FABP4, or anti-perilipin or anti-β3AR antibody. Finally, the specific immuno-reactive bands were developed with West-pico chemiluminescent substrate (Pierce Biotechnology, IL, USA), and the immunoblot images were captured in a Kodak Image Station (Kodak, USA). Band intensities were calculated densitometrically and normalized with expression of actin in respective samples. The data is summarized in FIG. 2.

The data manifested that the methanolic extract of Ficus hispida (LI/PD/044B/03) significantly modulated Peroxisome proliferator activated receptor gamma (PPARγ), CD36, adipocyte fatty acid binding protein 4 (FABP4 or aP2), Perilipin, and beta-3 Adrenergic Receptor (β3AR) in 3T3-L1 adipocytes.

Example 11

Figure 3:
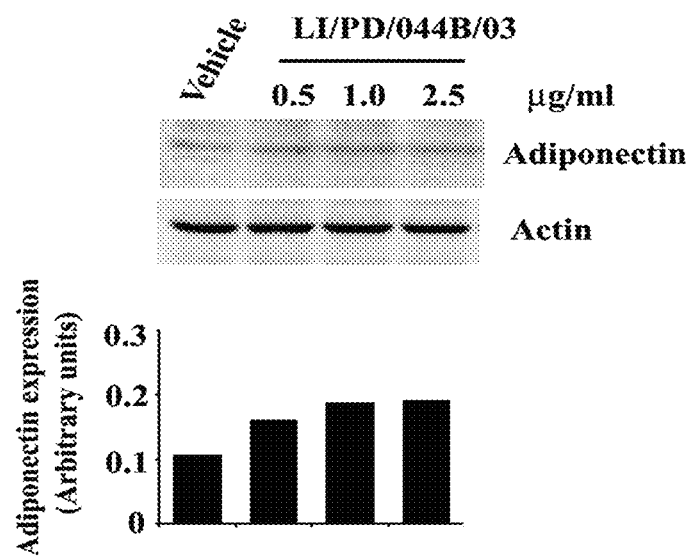
FIG. 3. Representative immunoblot showing dose dependent over expression of adiponectin protein in 3T3-L1 adipocytes treated at different concentrations of *Ficus hispida* methanol extract (LI/PD/044B/03). Protein expressions were densitometrically analyzed and normalized with the actin expression. Bar diagram shows normalized protein expressions in arbitrary units. The bars represent the levels of adiponectin in 3T3-L1 cells treated with vehicle control, 0.5 µg/ml, 1 µg/ml and 2.5 µg/ml of LI/PD/044B/03.

Upregulation of Adiponectin Production by Methanolic Extract of Ficus hispida (LI/PD/044B/03) in Mature Adipocytes Modulation of adiponectin protein by LI/PD/044B/03 in 3T3-L1 adipocytes was evaluated in Western immunoblot assay. The cell culture, treatment protocol and immunoblot assay methodology were the same as described in Example 10. FIG. 3 represents the upregulation of adiponectin protein expression in 3T3-L1 mature adipocytes by LI/PD/044B/03 in a dose dependent manner.

Example 12

Down Regulation of Protein Tyrosine Phosphatase-1B (PTP-1B) Activity in 3T3-L1 Preadipocytes by Methanolic Extract (LI/PD/044B/03) and 40% Aqueous Methanol Extract (LI/PD/044B/02) of Ficus hispida Leaves, and Methanolic Extract (LI/PD/044A/03) and 40% Aqueous Methanol Extract (LI/PD/044A/02) of Ficus hispida Fruits The 3T3-L1 preadipocytes were cultured in Dulbecco's Modified Eagle's Medium (DMEM) supplemented with 2 mM glutamine, 4.5 g/L glucose and 10% fetal bovine serum. Equal number of cells was plated in each well of 24-well cell culture plates. After overnight attachment, cells were incubated with different concentrations (1.0, 2.5 and 5.0 µg/ml) of LI/PD/044B/03 for 48 h. Vehicle treated cultures received only 0.1% DMSO. The wells were washed two times with chilled phosphate buffered saline and the cells were lysed with cell lysis buffer. The cell lysates were clarified at 14,000×g for 5 min at 4° C. The protein content was estimated by Bradford reagent. To evaluate the PTP-1B activity, 50 µl aliquots of cell lysates were reacted with equal volumes of substrate reagent containing 10 mM 4-nitrophenylphosphate (pNPP, Sigma Chemical Co., MO, USA) for 60 min at 37° C. The reaction was terminated by adding equal volume of 1N NaOH and the developed color was read at 405 nm in a microplate ELISA reader (BioRad, USA). The enzyme activity was calculated by using the following formula, where the extinction coefficient of pNPP at 405 nm is $1.78 \times 10^4$ $M^{-1} cm^{-1}$.

$$\frac{[(\text{Sample volume in liter}) \times A405]}{(\text{Extinction } coeff.) \times (\text{path length of light in cm}) \times (\text{time in min}) \times \text{protein(in } \mu g)}$$

FIG. 4 represents inhibition of PTP-1B activity by LI/PD/044B/03 in 3T3-L1 cells in a dose dependent manner.

The percentage inhibitions exhibited by the leaf and fruit extracts of Ficus hispida are summarized in Table 3.

TABLE 3

PTP 1B inhibitory activity of Ficus hispida

| Name of the test product | Treatment concentration | % inhibition of PTP 1B activity |
|---|---|---|
| LI/PD/044A/02 | 1 µg/mL | 11.31 |
|  | 2.5 µg/mL | 18.37 |
| LI/PD/044A/03 | 1 µg/mL | 12.96 |
|  | 2.5 µg/mL | 22.284 |
| LI/PD/044B/02 | 1 µg/ml | 20.99 |
|  | 2.5 µg/ml | 26.70 |
|  | 5 µg/ml | 44.24 |
| LI/PD/044B/03 | 1 µg/ml | 33.42 |
|  | 2.5 µg/ml | 41.84 |
|  | 5 µg/ml | 44.37 |

Example 13

Inhibition of CD36 Production by Methanolic Extract of Ficus hispida (LI/PD/044B/03) in in Vitro Atherosclerosis Model of High Glucose Induced Macrophage Cells Experimental protocol: This was evaluated in glucose induced J774, mouse macrophage cells. Briefly, the cells were cultured in DMEM with 2 mM Glutamine, 100 U/mL penicillin, 100 mg/mL streptomycin and 10% fetal bovine serum (Hyclone, Logan, Utah). Equal number of cells was seeded into 35 mm petri dishes (Corning, USA) one day before the experiment. The culture media was replaced with fresh, glucose free DMEM supplemented with 10% fetal bovine serum. *Ficus hispida* methanol extract (LI/PD/044B/03) at 1 µg/ml and 2.5 µg/ml was pre-incubated for 2 hours at 5% $CO_2$ at 37° C., and then co-incubated with 600 mg/dL of glucose for 5 days. The control culture was supplemented with 100 mg/dL glucose. The cells were harvested and lysed with lysis buffer. Cell lysates were clarified at 14,000 g. Protein concentration was measured by Bradford method.

Inhibition of CD36 protein expression in high glucose induced J774 macrophage cells in presence or absence of LI/PD/044B/03 was evaluated in immunoblot assay. Briefly, equal amount of cell lysates proteins was resolved in 7.5% SDS-PAGE; thereafter, the proteins were transferred to nitrocellulose membrane. After blocking the non-specific sites, the membrane was incubated with CD36 antibody (R&D Systems, Minneapolis, Minn.). Finally, the specific immunoreactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The results are summarized in FIG. 5.

Example 14

The Anti-Obesity Activity of the Methanol Extract of *Ficus hispida* (LI/PD/044B/03) was Tested Against High Fat Diet Induced Obesity Model of Sprague-Dawley Rats Induction: Selected healthy Sprague-Dawley rats were randomly assigned to control or various treatment groups (n=7). All the animals allocated to the obesity study were made experimentally obese through dietary intervention during the entire eight weeks induction period by feeding high fat diet ad libitum containing Bengal gram 32 g, Wheat floor 15 g, Yeast 1 g, Butter 2 g, Ground nut oil 8 g, Casein 5 g, Vanaspathi 20 g, Vitamin mix 05 g, Milk powder 12 g and Mineral Salt mixture 4.5 g per 100 g of high fat diet.

Treatment: Following 8 weeks of induction phase, the animals were treated orally (using oral feeding gavage) with either of the allocated test substances or vehicle daily for 8 weeks. The animals of treatment groups were supplemented with 100 mg/kg body weight of LI/PD/044B/03 or 250 mg/kg body weight of LI/PD/044B/03 or 7 mg/kg body weight of sibutramine in 10 mL of 0.5% CMC in water for further 8 weeks. The control group of animals received only the vehicle (10 mL of 0.5% CMC in water) during this period. During the treatment phase, all animals were provided with the standard rodent diet till the end of the study.

Body weights: Body weight of individual animal was recorded weekly during the entire duration of the study. Mean body weights for the treatment groups and control group were determined. The body weight gain was calculated at the end of 1st week, 4th week and 8th week after initiation of treatment in comparison to initial body weights. The percentage reduction in weight gain in the treatment groups was then calculated by comparing the weight gain in each treatment with that of control group. LI/PD/044B/03 inhibited the body weight gain in high fat diet induced obese rats. It exhibited 18.2% and 62.3% reduction in body weight gain in the treatment group supplemented with 100 mg/kg body weight and 250 mg/kg body weight of LI/PD/044B/03 respectively. The positive control sibutramine showed 40% reduction in weight gain when compared to the placebo. The results of body weight gain for the treatment groups and control group are summarized in FIG. 6.

Estimation of Biomarker Adiponectin: The serum adiponectin concentration for the control and treatment groups of animals were assessed using double antibody based sandwich rat adiponectin ELISA kit. The assay was performed following the instructions provided by the manufacturer (Linco Research, USA). The sensitivity of the assay is 0.155 ng/ml. Adiponectin assay revealed that supplementation of LI/PD/044B/03 at a dose of 250 mg/day/kg body weight for 8-weeks resulted in significant (p=0.00618) improvement (14.7%) in serum adiponectin concentration, in comparison with the baseline. The positive control sibutramine showed (6.3%) improvement in serum adiponectin concentration. The control group, however, showed 12% reduction in serum adiponectin concentration. The results are summarized in FIG. 7A.

Serum LDL concentration: The serum LDL levels in animals supplemented with different Treatments and control were estimated on Human Biochemistry Analyzer (German) and the results are summarized in FIG. 7B. The treatment groups supplemented with both the doses of LI/PD/044B/03 and the positive control sibutramine showed significant reduction in serum LDL concentrations.

Food and water consumption were recorded daily and fasting blood samples were collected before initiation, after 4th week and 8th week (termination) of the study.

Example 15

Bioactivity Guided Fractionation of Methanol Extract of *Ficus hispida* Leaves

A sample of 30 g of the methanol extract (LI/PD/044B/03) of the leaves of *Ficus hispida* described above was partitioned by successively:
  extracting the methanol extract (LI/PD/044B/03) with hexane (250 mL) to produce a hexane fraction and a first solid residue remaining after hexane extraction;
  extracting the first residue with ethyl acetate (250 mL) to produce an ethyl acetate fraction and a second residue remaining after ethyl acetate extraction; and
  extracting the second residue with methanol (250 mL) to produce a methanol fraction.

The hexane, ethyl acetate, and methanol fractions were evaporated separately under reduced pressure to obtain hexane extract (LI/PD/044B/03A; 8.25 g), ethylacetate extract (LI/PD/044B/03B; 2.70 g) and methanol extract (LI/PD/044B/03C, 16.5 g). The undissolved material was dried in a vacuum oven to obtain a residue (LI/PD/044B/04D; 1.5 g). The ethylacetate extract (LI/PD/044B/03B) and methanol extract (LI/PD/044B/03C) exhibited potent anti-adipogenesis activity and showed 94.3% and 64.5% inhibition of lipid accumulation respectively in 3T3-L1 mouse adipocyte cells. LI/PD/044B/03B and LI/PD/044B/03C also showed 47% and 116% acceleration of lipolysis respectively in 3T3-L1 mouse adipocytes cells as indicated by the percentage increase glycerol release into the culture medium. The active extract LI/PD/044B/03C (5 g) obtained in major proportion was then subjected to gel filtration chromatography on Sephadex LH20 using methanol as an eluant. Ten fraction of each 250 mL were collected. Based on TLC pattern the fractions 1 and 2 were combined labeled as LI/PD/044B/03C/1). The fraction 3, 4 and 5 are kept separate and labeled as LI/PD/044B/03C/2 (130.2 mg), LI/PD/044B/03C/3 (1630 mg) and LI/PD/044B/03C/4 (883 mg) respectively. The fractions 6, 7 and 8 were combined to obtain LI/PD/044B/03C/5 (528 mg) and fractions 9 and 10 were combined into LI/PD/044B/03C/6 (129 mg). The fractions were evaporated individually. The fractions LI/PD/044B/03C/3 and LI/PD/044B/03C/4 showed potent anti-adipogenesis activity and prolipolysis activities in 3T3-L1 mouse adipocyte cells. LI/PD/044B/03C/3 and LI/PD/044B/03C/4 showed 109% and 111.5% inhibition of lipid accumulation in differentiated adipocytes respectively at 1 µg/mL concentration. Similarly, fractions LI/PD/044B/03C/3 and LI/PD/044B/03C/4 accelerated lipolysis by 107.6% and 190.6% respectively in mature adipocytes. The flow diagram for the fractionation is summarized in FIG. 8. The anti-adipogenic activity and prolipolytic activity of the fractions are summarized in Table 4.

TABLE 4

Anti-adipogenic and prolipolytic activities of the fractions obtained from methanolic extract the leaves of Ficus hispida

| Name of the test product | % inhibition of adipogenesis | % acceleration of lipolysis |
|---|---|---|
| LI/PD/044B/03 | 30.23% at 0.5 µg/ml | 38.35% at 25 µg/ml |
|  | 52.33% at 1 µg/ml | 47.02% at 50 µg/ml |
| LI/PD/044B/03A | 13.7% at 0.5 µg/ml | 0% at 25 µg/ml |
|  | 15.32% at 1 µg/ml | 50.15% at 50 µg/ml |
| LI/PD/044B/03B | 21.77% at 0.5 µg/ml | <0% at 25 µg/ml |
|  | 94.35% at 1 µg/ml | 47.02% at 50 µg/ml |
| LI/PD/044B/03C | — | 38.34% at 25 µg/ml |
|  | 64.52% at 1 µg/ml | 115.98% at 50 µg/ml |
| LI/PD/044B/03D | <0% at 0.5 µg/ml | 76.19% at 25 µg/ml |
|  | <0% at 1 µg/ml | 50.15% at 50 µg/ml |
| LI/PD/044B/03C/01 | <0% at 0.5 µg/ml | <0% at 25 µg/ml |
|  | <0% at 1 µg/ml | <0% at 50 µg/ml |
| LI/PD/044B/03C/02 | <0% at 0.5 µg/ml | <0% at 25 µg/ml |
|  | <0% at 1 µg/ml | <0% at 50 µg/ml |
| LI/PD/044B/03C/03 | 82.05% at 0.5 µg/ml | 77.36% at 25 µg/ml |
|  | 108.97% at 1 µg/ml | 107.55% at 50 µg/ml |
| LI/PD/044B/03C/04 | 85.04% at 0.5 µg/ml | 92.45% at 25 µg/ml |
|  | 111.53% at 1 µg/ml | 190.57% at 50 µg/ml |
| LI/PD/044B/03C/05 | 11.96% at 0.5 µg/ml | <0% at 25 µg/ml |
|  | 43.58% at 1 µg/ml | 9.45% at 50 µg/ml |
| LI/PD/044B/03C/06 | <0% at 0.5 µg/ml | <0% at 25 µg/ml |
|  | 4.27% at 1 µg/ml | <0% at 50 µg/ml |

Example 16

Inhibition of Tumor Necrosis Factor-α (TNF-α) In Vitro by Extracts, Fractions and Compounds of *Ficus hispida*

The anti-inflammatory activities of extracts and fractions of *Ficus hispida* were assessed in a cell based in vitro assay. Briefly, THP-1 human monocytes cells were washed and re-suspended in phenol red free Dulbecco's Modified Eagle's Medium (DMEM) supplemented with 1% fetal Bovine serum (FBS). Equal number of cells was added to each well of a 96-well TC plate and the cells were pretreated for 2 h with various concentrations (ranging from 0.1 to 200 µg/mL; solutions prepared in culture medium from a stock solution containing 50 mg/1 mL DMSO of each test compound) of extracts and fractions of *Ficus hispida*. The inflammatory response was induced by 100 ng/mL of LPS for 4 h at 37° C. in presence of 5% $CO_2$. The vehicle control culture wells received 0.1% DMSO in culture medium. The cell culture supernatants were collected and assessed for secretory pro-inflammatory cytokine, TNFα. The TNFα concentration was quantitatively measured by highly specific and sensitive Enzyme Immuno Assay (EIA) kit supplied by R&D Systems, USA. The enzyme immuno assay was performed based on the protocol provided by the vendor. The percentage inhibition of TNFα at 5 µg/mL concentration of each product was calculated by comparison with TNFα level in the cells treated with the control. Table 5 is a summary of percentage inhibition of TNFα 5 µg/mL concentration of various extracts and fractions of *Ficus hispida* in cell based in vitro model.

TABLE 5

Anti-TNFα Activity of the extract of *F. hispida*

| Compound code | % TNFα inhibition at 5 µg/mL |
|---|---|
| LI/PD/044B/02 | 46.8 |
| LI/PD/044B/03 | 51.7 |
| LI/PD/044B/03A | 7.4 |
| LI/PD/044B/03B | 59.1 |
| LI/PD/044B/03C | 46.8 |
| LI/PD/044B/03D | 34.5 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A method of treating a metabolic disorder in a patient in need thereof comprising:
    a) obtaining an organic solvent extract of *Ficus hispida* leaves or *Ficus hispida* fruit; and
    b) administering an effective amount of said organic solvent extract of *Ficus hispida* leaves or *Ficus hispida* fruit to said patient;
    wherein the metabolic disorder is selected from the group consisting of obesity, low HDL cholesterol, high triglycerides, diabetes, impaired fasting glucose, dyslipidemia, high total cholesterol, atherosclerosis and hyperglycemia.

2. The method of claim 1, wherein said organic solvent extract of *Ficus hispida* leaves or *Ficus hispida* fruit is obtained by extraction of *Ficus hispida* leaves or *Ficus hispida* fruit with an organic solvent selected from the group consisting of: hexane, dichloromethane, chloroform, ethyl acetate, acetone, methanol, ethanol, n-butanol, isopropanol, methyl isobutyl ketone, aqueous methanol or a mixture thereof.

3. A method of treating a metabolic disorder in a patient in need thereof comprising:
    administering an effective amount of an organic solvent extract of *Ficus hispida* leaves or *Ficus hispida* fruit to said patient,
    wherein the metabolic disorder is selected from the group consisting of: obesity, low HDL cholesterol, high triglycerides, diabetes, impaired fasting glucose, dyslipidemia, high total cholesterol, atherosclerosis and hyperglycemia, and
    wherein said organic solvent extract is selected from the group consisting of: an ethyl acetate extract of *Ficus hispida* or leaves, a methanol extract of *Ficus hispida* fruit or leaves, a hydroalcoholic extract of *Ficus hispida* fruit or leaves or a mixture thereof.

4. The method of claim 1, wherein said organic solvent extract of *Ficus hispida* leaves or *Ficus hispida* fruit is orally, topically or parenterally administered or administered by inhalation.

5. The method of claim 1, wherein said organic solvent extract of *Ficus hispida* leaves or *Ficus hispida* fruit is administered at least once daily.

6. The method of claim 2, wherein said organic solvent is selected from the group consisting of ethyl acetate, methanol, and aqueous methanol.

7. The method of claim 1, wherein said at least one symptom comprises obesity.

8. The method of claim 1, wherein said organic solvent extract of *Ficus hispida* leaves or *Ficus hispida* fruit is obtained by:
   i) extracting *Ficus hispida* leaves with alcohol to produce a first extract, followed by sequentially:
   ii) extracting said first extract with hexane to produce a second hexane extract and a first residue;
   iii) optionally extracting said first residue with ethyl acetate to produce a third ethyl acetate extract and a second residue; and
   iv) optionally extracting said second residue with alcohol to produce a fourth alcohol extract;
   wherein said organic solvent extract is selected from the group consisting of said second hexane extract, said third ethyl acetate extract; and said fourth alcohol extract.

9. The method of claim 8, wherein said second hexane extract, said third ethyl acetate extract, or said fourth methanol extract is administered to said patient in an amount effective to accelerate lipolysis; or
   wherein said third ethyl acetate extract or said fourth methanol extract is administered to said patient in an amount effective to inhibit adipogenesis.

10. The method of claim 1, comprising:
    administering said effective amount of said organic solvent extract of *Ficus hispida* fruit to said patient, wherein said administration of the organic solvent extract of *Ficus hispida* fruit inhibits lipid accumulation or stimulates lypolysis in said patient.

11. The method of claim 1, comprising:
    administering said effective amount of said organic solvent extract of *Ficus hispida* to said patient;
    wherein said organic solvent extract of *Ficus hispida* is a non-alcoholic extract of *Ficus hispida* leaves or an extract of *Ficus hispida* fruit, wherein said administration of the organic solvent extract of *Ficus hispida* inhibits lipid accumulation or stimulates lypolysis in said patient.

12. The method of claim 11, wherein said organic solvent extract of *Ficus hispida* is an ethyl acetate extract of *Ficus hispida* fruit, a methanol extract of *Ficus hispida* fruit, a hydroalcoholic extract of *Ficus hispida* fruit, an ethyl acetate extract of *Ficus hispida* leaves, or a mixture thereof.

13. The method of claim 1, wherein said at least one symptom is atherosclerosis.

14. The method of claim 1, wherein said at least one symptom is diabetes.

15. The method of claim 1, comprising:
    administering said effective amount of said organic solvent extract of *Ficus hispida* to said patient;
    wherein said organic solvent extract of *Ficus hispida* is a non-alcoholic extract of *Ficus hispida* leaves or an extract of *Ficus hispida* fruit, wherein said administration of the organic solvent extract of *Ficus hispida* leaves or fruit stimulates adiponectin production in said patient.

16. The method of claim 1, comprising:
    administering said effective amount of said organic solvent extract of *Ficus hispida* to said patient;
    wherein said organic solvent extract of *Ficus hispida* is a non-alcoholic extract of *Ficus hispida* leaves or an extract of *Ficus hispida* fruit, wherein said administration of the organic solvent extract of *Ficus hispida* leaves or fruit ameliorates an inflammatory biomarker protein or molecule in said patient, and
    wherein said inflammatory biomarker protein or molecule is selected from the group consisting of TNFα, IL-Iβ, IL-6, MMP-3 and NFκB, whose expression is altered during inflammatory conditions.

* * * * *